US010456480B2

(12) United States Patent
Poeschla et al.

(10) Patent No.: US 10,456,480 B2
(45) Date of Patent: *Oct. 29, 2019

(54) TREATING GLAUCOMA, CARDIOVASCULAR DISEASES, AND RENAL DISEASES

(71) Applicant: Mayo Foundation for Medical Education and Research, Rochester, MN (US)

(72) Inventors: Eric M. Poeschla, Rochester, MN (US); Roman A. Barraza, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,180

(22) Filed: Jul. 30, 2018

(65) Prior Publication Data

US 2018/0326016 A1 Nov. 15, 2018

Related U.S. Application Data

(63) Continuation of application No. 15/187,471, filed on Jun. 20, 2016, now Pat. No. 10,058,597, which is a continuation of application No. 14/510,921, filed on Oct. 9, 2014, now Pat. No. 9,393,322, which is a continuation of application No. 13/624,383, filed on Sep. 21, 2012, now Pat. No. 8,871,733, which is a continuation of application No. 12/298,431, filed as application No. PCT/US2007/067710 on Apr. 27, 2007, now Pat. No. 8,299,043.

(60) Provisional application No. 60/795,789, filed on Apr. 28, 2006.

(51) Int. Cl.
| | | |
|---|---|---|
| A61K 48/00 | (2006.01) | |
| A61K 38/44 | (2006.01) | |
| A61K 38/00 | (2006.01) | |
| C12N 9/02 | (2006.01) | |

(52) U.S. Cl.
CPC ............ *A61K 48/00* (2013.01); *A61K 38/44* (2013.01); *A61K 48/005* (2013.01); *C12N 9/0083* (2013.01); *C12Y 114/99001* (2013.01); *A61K 38/00* (2013.01); *C12N 2799/04* (2013.01)

(58) Field of Classification Search
CPC ...... A61K 48/00; A61K 38/44; A61K 48/005; A61K 38/00; C12N 9/0083; C12N 2799/04; C12Y 114/99001
USPC .................. 514/44 R; 424/199.1; 435/320.1
See application file for complete search history.

(56) References Cited

U.S. PATENT DOCUMENTS

| | | | |
|---|---|---|---|
| 5,543,297 A | 8/1996 | Cromlish et al. | |
| 5,676,954 A | 10/1997 | Brigham | |
| 5,705,150 A | 1/1998 | Risser | |
| 6,124,115 A | 9/2000 | Labrie | |
| 6,362,327 B1 | 3/2002 | O'Neill et al. | |
| 6,638,744 B2 | 10/2003 | Wisnewski et al. | |
| 7,510,851 B2 | 3/2009 | Waters | |
| 8,299,043 B2* | 10/2012 | Poeschla ............. | A61K 48/005 514/44 R |
| 8,871,733 B2* | 10/2014 | Poeschla ............. | A61K 48/005 514/44 R |
| 9,393,322 B2* | 7/2016 | Poeschla ............. | A61K 48/005 |
| 2002/0035264 A1 | 3/2002 | Kararli et al. | |
| 2002/0107219 A1 | 8/2002 | Curiel et al. | |
| 2002/0168739 A1 | 11/2002 | Wu | |
| 2004/0234505 A1 | 11/2004 | Naylor et al. | |

OTHER PUBLICATIONS

Maihofner et al. IOVS 2001;42:2616-24.*
Hinz et al. FASEB J, express article 10.1096;Online Aug. 2, 2005, pp. 1-24.*
Martin et al. Methods 2002;28:267-75.*
Lu et al. Int. J. Cancer 2005;116:847-852.*
Camras and Podos, "The role of endogenous prostaglandins in clinically-used and investigational glaucoma therapy," *The Ocular Effects of Prostaglandins and Other Eicosanoids*, Alan R. Liss, Inc. 1989, pp. 459-475, 1989.
Cheever, "An overview of pulmonary arterial hypertension: risks, pathogenesis, clinical manifestations, and management," *J. Cardiovasc. Nursing*, 20(2):108-116, Mar.-Apr. 2005.
Farley et al. Am J Vet Res 200566:1985-1991.
Fetalvero et al., "Cardioprotective prostacyclin signaling in vascular smooth muscle," *Prostaglandins Other Lipid Mediat.*, 82(1-4):109-118, Epub Jul. 7, 2006.
GenBank® GI No. GI:2493373 (Q16647) dated Jan. 20, 2009, 9 pages.
GenBank® GI No. GI:39995095 (NM_000960) dated Jan. 25, 2009, 4 pages.
GenBank® GI No. GI:4506263 (NP_000951) dated Jan. 25, 2009, 4 pages.
GenBank® GI No. GI:75517290 (BC101811) dated Jul. 21, 2006, 3 pages.
Hinz et al., "Latanoprost induces matrix metalloproteinase-1 expression in human nonpigmented ciliary epithelial cells through a cyclooxygenase-2-dependent mechanism," *FASEB J.*, 19(13):1929-1931, Epub Aug. 2, 2005.
Kunapuli et al., "Functional characterization of the ocular prostaglandin f2alpha (PGF2alpha) receptor. Activation by the isoprostane, 12-iso-PGF2alpha," *J Biol Chem.*, 272(43):27147-27154, Oct. 24, 1997.

(Continued)

*Primary Examiner* — Anne Marie S Wehbe
(74) *Attorney, Agent, or Firm* — Fish & Richardson P.C.

(57) ABSTRACT

This document provides methods and materials related to treating glaucoma, ocular hypertension, cardiovascular diseases, and renal diseases. For example, this document provides isolated nucleic acid molecules and viral vectors (e.g., lentiviral vectors) containing isolated nucleic acid molecules. Methods for reducing intraocular pressure as well as symptoms and progression of cardiovascular and renal diseases also are provided.

8 Claims, 18 Drawing Sheets

Specification includes a Sequence Listing.

(56) References Cited

OTHER PUBLICATIONS

Loewen et al. Hum Gene Ther 2001;12:2109-19.
Loewen et al., "FIV Vectors," *Meth. Mol. Biol.*, 229:251-271, 2003.
Loewen et al., "Preservation of aqueous outflow facility after second-generation FIV vector-mediated expression of marker genes in anterior segments of human eyes," *Invest Ophthalmol Vis Sci.*, 43(12):3686-3690, Dec. 2002.
Lu et al., "Cyclooxygenase-2 overexpression in MCF-10F human breast epithelial cells inhibits proliferation, apoptosis and differentiation, and causes partial transformation," *Int J Cancer.*, 116(6):847-852, Oct. 10, 2005.
Maihöfner et al., "Expression of cyclooxygenase-1 and -2 in normal and glaucomatous human eyes," *Invest Ophthalmol Vis Sci.*, 42(11):2616-2624, Oct. 2001.
Mandal et al., "Uteroglobin inhibits prostaglandin F2alpha receptor-mediated expression of genes critical for the production of pro-inflammatory lipid mediators," *J Biol Chem.*, 280(38):32897-32904, Epub Aug. 1, 2005.
Martin et al. "Gene delivery to the eye using adeno-associated viral vectors," *Methods* 28(2):267-275, Oct. 2002.
Nakajima et al., "New fluoroprostaglandin F(2alpha) derivatives with prostanoid FP-receptor agonistic activity as potent ocular-hypotensive agents," *Biol Pharm Bull.*, 26(12):1691-1695, Dec. 2003.
Nakashima et al. Biochimica et Biophysica Acta 2003;1633:96-105.
Nasrallah and Hébert, "Prostacyclin signaling in the kidney: implications for health and disease," *Am. J. Physiol. Renal Physiol.*, 289(2):F235-F246, Aug. 2005.
Poeschla et al., "Efficient transduction of nondividing human cells by feline immunodeficiency virus lentiviral vectors," *Nat. Med.*, 4(3):354-357, Mar. 1998.
Rösch et al., "Prostaglandin E2 induces cyclooxygenase-2 expression in human non-pigmented ciliary epithelial cells through activation of p38 and p42/44 mitogen-activated protein kinases," *Biochem Biophys Res Commun.*, 338(2):1171-1178, Epub Oct. 21, 2005.
Saenz et al., "Restriction of feline immunodeficiency virus by Ref1, Lv1, and primate TRIM5alpha proteins," *J. Virol.*, 79(24):15175-15188, Dec. 2005.
Vassalli and Dichek, "Gene therapy for arterial thrombosis," *Cardiovasc. Res.*, 35:459-469, 1997.
Authorized Officer I. S. Yang. International Search Report and Written Opinion in International Application No. PCT/US2007/067710, dated Sep. 21, 2007, 13 pages.
Authorized Officer E. Moyse. International Preliminary Report on Patentability in International Application No. PCT/US2007/067710, dated Nov. 6, 2008, 7 pages.

\* cited by examiner

Figure 3
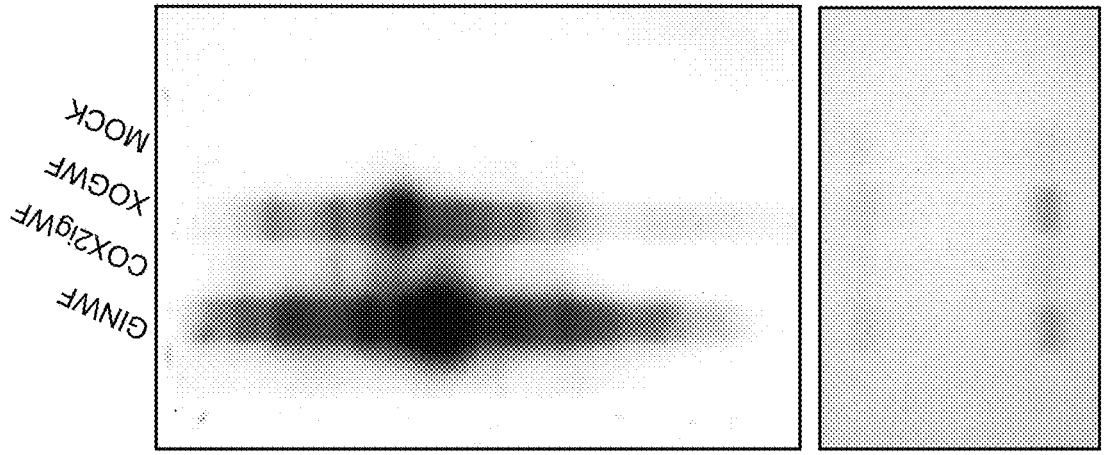
Random-labeled (32P-dCTP) GFP probe
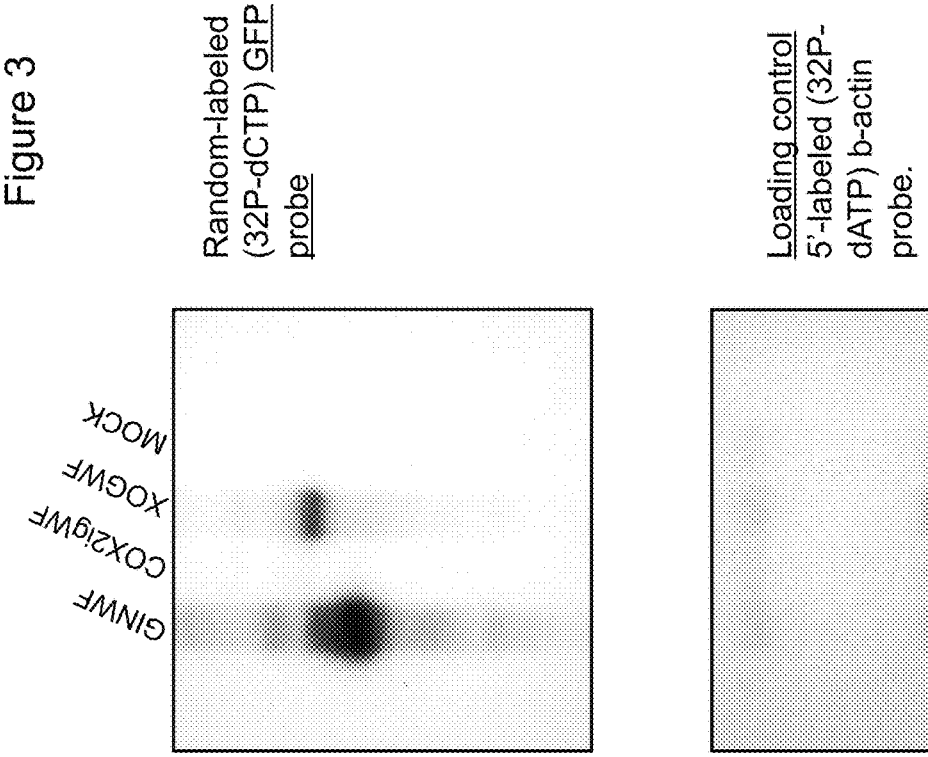
Loading control 5'-labeled (32P-dATP) b-actin probe.

Figure 8

| Cat (right eye) | Group | COX-2 | PGFS | FPR | GINWF | Total Volume (ul) |
|---|---|---|---|---|---|---|
| 1 J168 | COX-2 | 1 x 10⁷ TU | | | | 200 |
| 2 J114 | | 1 x 10⁷ TU | | | | 200 |
| 3 J108 | | 1 x 10⁷ TU | | | | 200 |
| 4 J210 | COX-2 PGFS | 1 x 10⁷ TU | 1 x 10⁷ TU | | | 200 |
| 5 J134 | | 1 x 10⁷ TU | 1 x 10⁷ TU | | | 200 |
| 6 J150 | | 1 x 10⁷ TU | 1 x 10⁷ TU | | | 200 |
| 7 J212 | COX-2 PGFS FPR | 1 x 10⁷ TU | 1 x 10⁷ TU | 1 x 10⁷ TU | | 200 |
| 8 J236 | | 1 x 10⁷ TU | 1 x 10⁷ TU | 1 x 10⁷ TU | | 200 |
| 9 J160 | | 1 x 10⁷ TU | 1 x 10⁷ TU | 1 x 10⁷ TU | | 200 |
| 10 J118 | COX-2 FPR | 1 x 10⁷ TU | | 1 x 10⁷ TU | | 200 |
| 11 J264 | | 1 x 10⁷ TU | | 1 x 10⁷ TU | | 200 |
| 12 J166 | | 1 x 10⁷ TU | | 1 x 10⁷ TU | | 200 |
| 13 J172 | FPR | | | 1 x 10⁷ TU | | 200 |
| 14 J116 | | | | 1 x 10⁷ TU | | 200 |
| 15 K004 | | | | 1 x 10⁷ TU | | 200 |
| Left Eyes | GINWF | | | | 1 x 10⁷ TU | 200 |

*1 x 10⁷ TU each vector delivered to anterior chamber of cat eye via transcorneal injection.

Figure 11

```
MLARALLLCAVLALSHTANPCCSHPCQNRGVCMSVGFDQYKCDCTRTGFYGENCSTPEFLTRIK
LFLKPTPNTVHYILTHFKGFWNVVNNIPFLRNAIMSYVLTSRSHLIDSPPTYNADYGYKSWEAF
SNLSYYTRALPPVPDDCPTPLGVKGKKQLPDSNEIVEKLLLRRKFIPDPQGSNMMFAFFAQHFT
HQFFKTDHKRGPAFTNGLGHGVDLNHIYGETLARQRKLRLFKDGKMKYQIIDGEMYPPTVKDTQ
AEMIYPPQVPEHLRFAVGQEVFGLVPGLMMYATIWLREHNRVCDVLKQEHPEWGDEQLFQTSRL
ILIGETIKIVIEDYVQHLSGYHFKLKFDPELLFNKQFQYQNRIAAEFNTLYHWHPLLPDTFQIH
DQKYNYQQFIYNNSILLEHGITQFVESFTRQIAGRVAGGRNVPPAVQKVSQASIDQSRQMKYQS
FNEYRKRFMLKPYESFEELTGEKEMSAELEALYGDIDAVELYPALLVEKPRPDAIFGETMVEVG
APFSLKGLMGNVICSPAYWKPSTFGGEVGFQIINTASIQSLICNNVKGCPFTSFSVPDPELIKT
VTINASSSRSGLDDINPTVLLKERSTEL
```

Figure 12

```
ATGCTCGCCCGCGCCCTGCTGCTGTGCGCGGTCCTGGCGCTCAGCCATACAGCAAATCCTTGCTGTTCCCACCCATGT
CAAAACCGAGGTGTATGTATGAGTGTGGGATTTGACCAGTATAAGTGCGATTGTACCCGGACAGGATTCTATGGAGAA
AACTGCTCAACACCGGAATTTTTGACAAGAATAAAATTATTTCTGAAACCCACTCCAAACACAGTGCACTACATACTT
ACCCACTTCAAGGGATTTTGGAACGTTGTGAATAACATTCCCTTCCTTCGAAATGCAATTATGAGTTATGTCTTGACA
TCCAGATCACATTTGATTGACAGTCCACCAACTTACAATGCTGACTATGGCTACAAAAGCTGGGAAGCCTTCTCTAAC
CTCTCCTATTATACTAGAGCCCTTCCTCCTGTGCCTGATGATTGCCCGACTCCCTTGGGTGTCAAAGGTAAAAGCAG
CTTCCTGATTCAAATGAGATTGTGGAAAAATTGCTTCTAAGAAGAAAGTTCATCCCTGATCCCCAGGGCTCAAACATG
ATGTTTGCATTCTTTGCCCAGCACTTCACGCATCAGTTTTTCAAGACAGATCATAAGCGAGGGCCAGCTTTCACCAAC
GGGCTGGGCCATGGGGTGGACTTAAATCATATTTACGGTGAAACTCTGGCTAGACAGCGTAAACTGCGCCTTTTCAAG
GATGGAAAAATGAAATATCAGATAATTGATGGAGAGATGTATCCTCCCACAGTCAAAGATACTCAGGCAGAGATGATC
TACCCTCCTCAAGTCCCTGAGCATCTACGGTTTGCTGTGGGCAGGAGGTCTTTGGTCTGGTGCCTGGTCTGATGATG
TATGCCACAATCTGGCTGCGGGAACACAACAGAGTATGCGATGTGCTTAAACAGGAGCATCCTGAATGGGGTGATGAG
CAGTTGTTCCAGACAAGCAGGCTAATACTGATAGGAGAGACTATTAAGATTGTGATTGAAGATTATGTGCAACACTTG
AGTGGCTATCACTTCAAACTGAAATTTGACCCAGAACTACTTTTCAACAAACAATTCCAGTACCAAAATCGTATTGCT
GCTGAATTTAACACCCTCTATCACTGGCATCCCCTTCTGCCTGACACCTTTCAAATTCATGACCAGAAATACAACTAT
CAACAGTTTATCTACAACAACTCTATATTGCTGGAACATGGAATTACCCAGTTTGTTGAATCATTCACCAGGCAAATT
GCTGGCAGGGTTGCTGGTGGTAGGAATGTTCCACCCGCAGTACAGAAAGTATCACAGGCTTCCATTGACCAGAGCAGG
CAGATGAAATACCAGTCTTTTAATGAGTACCGCAAACGCTTTATGCTGAAGCCCTATGAATCATTTGAAGAACTTACA
GGAGAAAAGGAAATGTCTGCAGAGTTGGAAGCACTCTATGGTGACATCGATGCTGTGGAGCTGTATCCTGCCCTTCTG
GTAGAAAAGCCTCGGCCAGATGCCATCTTTGGTGAAACCATGGTAGAAGTTGGAGCACCATTCTCCTTGAAAGGACTT
ATGGGTAATGTTATATGTTCTCCTGCCTACTGGAAGCCAAGCACTTTTGGTGGAGAAGTGGGTTTTCAAATCATCAAC
ACTGCCTCAATTCAGTCTCTCATCTGCAATAACGTGAAGGGCTGTCCCTTTACTTCATTCAGTGTTCCAGATCCAGAG
CTCATTAAAACAGTCACCATCAATGCAAGTTCTTCCCGCTCCGGACTAGATGATATCAATCCCACAGTACTACTAAAA
GAACGTTCGACTGAACTGTAG
```

Figure 13

```
ATGCTCGCTCGGGCTCTGCTCCTGTGCGCTGTGCTGGCTCTCAGCCACACCGCTAACCCCTGCTGCAGCCACCCCTGC
CAGAACCGGGGCGTGTGCATGAGCGTGGGCTTCGACCAGTACAAGTGCGATTGCACCCGGACCGGCTTCTACGGCGAA
AACTGCAGCACCCCCGAGTTCCTGACCCGGATCAAACTGTTCCTGAAACCCACCCCCAACACCGTGCACTACATCCTG
ACCCACTTCAAGGGCTTCTGGAACGTGGTGAACAACATCCCCTTCCTGCGGAACGCTATCATGAGCTACGTGCTGACC
AGCCGGAGCCACCTGATCGATAGCCCTCCCACCTACAACGCTGACTACGGCTACAAAAGCTGGGAAGCCTTCAGCAAC
CTCAGCTACTACACCCGGGCTCTGCCTCCCGTGCCCGATGATTGCCCCACCCCTCTGGGCGTGAAAGGCAAGAAGCAG
CTGCCCGATAGCAACGAGATCGTGGAAAAACTGCTCCTGCGGCGGAAGTTCATCCCCGATCCCCAGGGCAGCAACATG
ATGTTCGCTTTCTTCGCCCAGCACTTCACCCCACCAGTTCTTCAAGACCGATCACAAACGGGGCCCCGCCTTCACCAAC
GGCCTGGGCCACGGCGTGGACCTGAACCACATCTACGGCGAAACCCTGGCTCGGCAGCGGAAACTGCGGCTGTTCAAG
GATGGCAAAATGAAATACCAGATCATCGATGGCGAGATGTACCCTCCCACCGTGAAAGATACCCAGGCTGAAATGATC
TACCCCCCCCAGGTGCCCGAACACCTGCGGTTCGCTGTGGGCCAGGAAGTGTTCGGCCTGGTGCCCGGCCTGATGATG
TACGCTACCATCTGGCTGCGGGAACACAACCGGGTGTGCGATGTGCTGAAACAGGAACACCCCGAATGGGGCGATGAA
CAGCTGTTCCAGACCAGCCGGCTGATCCTGATCGGCGAGACCATCAAGATCGTGATCGAAGATTACGTGCAGCACCTG
AGCGGCTACCACTTCAAACTGAAATTCGACCCCGAACTGCTCTTCAACAAACAGTTCCAGTACCAGAACCGGATCGCT
GCCGAGTTCAACACCCTCTACCACTGGCACCCCCTGCTCCCGACACCTTCCAGATCCACGACCAGAAATACAACTAC
CAGCAGTTCATCTACAACAACAGCATCCTGCTCGAACACGGCATCACCCAGTTCGTGGAAAGCTTCACCCGGCAGATC
GCTGGCCGGGTGGCTGGCGGCCGGAACGTGCCTCCTGCCGTGCAGAAAGTGAGCCAGGCTAGCATCGACCAGAGCCGG
CAGATGAAATACCAGAGCTTCAACGAGTACCGGAAACGGTTCATGCTGAAGCCCTACGAAAGCTTCGAAGAGCTGACC
GGCGAAAAGGAAATGAGCGCTGAACTGGAAGCTCTGTACGGCGACATCGATGCTGTGGAACTGTACCCCGCCCTCCTG
GTGGAGAAACCCCGGCCCGATGCCATCTTCGGCGAAACCATGGTGGAAGTGGGCGCTCCCTTCAGCCTGAAAGGCCTG
ATGGGCAACGTGATCTGCAGCCCCGCTTACTGGAAACCCAGCACCTTCGGCGGCGAAGTGGGCTTCCAGATCATCAAC
ACCGCCAGCATCCAGAGCCTCATCTGCAACAACGTGAAAGGCTGCCCCTTCACCAGCTTCAGCGTGCCCGATCCCGAG
CTCATCAAAACCGTGACCATCAACGCTAGCAGCAGCCGGAGCGGCCTGGATGACATCAACCCCACCGTGCTGCTCAAA
GAACGGAGCACCGAACTGTGA
```

Figure 14

MYPYDVPDYASMNNSKQLVSPAAALLSNTTCQTENRLSVFFSVIFMTVGILSNSLAIAILMKAY
QRFRQKSKASFLLLASGLVITDFFGHLINGAIAVFVYASDKEWIRFDQSNVLCSIFGICMVFSG
LCPLLLGSVMAIERCIGVTKPIFHSTKITSKHVKMMLSGVCLFAVFIALLPILGHRDYKIQASR
TWCFYNTEDIKDWEDRFYLLLFSFLGLLALGVSLLCNAITGITLLRVKFKSQQHRQGRSHHLEM
VIQLLAIMCVSCICWSPFLVTMANIGINGNHSLETCETTLFALRMATWNQILDPWVYILLRKAV
LKNLYKLASQCCGVHVISLHIWELSSIKNSLKVAAISESPVAEKSAST

Figure 15

```
atgTATCCATATGATGTGCCAGATTATGCTtccatgaacaattccaaacagctagtgtctcctgcagctgcgcttctt
tcaaacacaacctgccagacggaaaaccggctttccgtattttttcagtaatcttcatgacagtgggaatcttgtca
aacagccttgccatcgccattctcatgaaggcatatcagagatttagacagaagtccaaggcatcgtttctgcttttg
gccagcggcctggtaatcactgatttctttggccatctcatcaatggagccatagcagtatttgtatatgcttctgat
aaagaatggatccgctttgaccaatcaaatgtcctttgcagtattttggtatctgcatggtgttttctggtctgtgc
ccacttcttctaggcagtgtgatggccattgagcggtgtattggagtcacaaaaccaatatttcattctacgaaaatt
acatccaaacatgtgaaaatgatgttaagtggtgtgtgcttgtttgctgttttcatagctttgctgcccatccttgga
catcgagactataaaattcaggcgtcgaggacctggtgtttctacaacacagaagacatcaaagactgggaagataga
tttatcttctactttttctttctttctggggctcttagcccttggtgtttcattgttgtgcaatgcaatcacaggaatt
acacttttaagagttaaatttaaaagtcagcagcacagacaaggcagatctcatcatttggaaatggtaatccagctc
ctggcgataatgtgtgtctcctgtatttgttggagcccatttctggttacaatggccaacattggaataaatggaaat
cattctctggaaacctgtgaaacaacacttttttgctctccgaatggcaacatggaatcaaatcttagatccttgggta
tatattcttctacgaaaggctgtccttaagaatctctataagcttgccagtcaatgctgtggagtgcatgtcatcagc
ttacatatttgggagcttagttccattaaaaattccttaaaggttgctgctatttctgagtcaccagttgcagagaaa
tcagcaagcacctag
```

Figure 16 atgTA<u>C</u>CC<u>C</u>TATGA<u>C</u>GTGCCAGATTA<u>C</u>GC<u>C</u>tccatgaacaattccaaacagct<u>c</u>gtgtc<u>a</u>cc<u>c</u>gcagctgc<u>a</u>ctgct<u>c</u>
tc<u>t</u>a<u>a</u>t<u>a</u>caac<u>a</u>tgccagac<u>c</u>gagaa<u>t</u>Aggct<u>cAg</u>cgtg<u>t</u>ttttctc<u>t</u>g<u>a</u>tctttatgactg<u>t</u>ggg<u>c</u>atc<u>c</u>t<u>cAgc</u>
aac<u>tcA</u>ct<u>gg</u>c<u>t</u>atcgc<u>a</u>attctgatgaaggc<u>c</u>ta<u>cc</u>ag<u>c</u>g<u>c</u>ttt<u>c</u>gacagaaga<u>gt</u>aaggc<u>c</u>tc<u>t</u>tt<u>c</u>ct<u>c</u>ct<u>g</u>c<u>t</u>g
gccagc<u>ggg</u>ctggt<u>c</u>at<u>t</u>a<u>cc</u>ga<u>c</u>tttt<u>t</u><u>c</u>gga<u>c</u>a<u>cc</u>tcatcaatggagc<u>a</u>t<u>tgc</u>t<u>g</u>t<u>g</u>tt<u>c</u>g<u>t</u><u>c</u>tatgc<u>c</u>t<u>cc</u>gat
aaggagtggat<u>t</u>aga<u>t</u>t<u>c</u>gatcagtcaaa<u>c</u>gtgc<u>t</u><u>c</u>tg<u>t</u><u>t</u><u>c</u>aat<u>c</u>tttggtatctg<u>t</u>atggt<u>c</u>ttttc<u>a</u>ggtct<u>c</u>tgc
cctctgctgct<u>g</u>ggc<u>t</u><u>cc</u>gtgatggccattgagc<u>g</u><u>c</u>tgtattggc<u>g</u>t<u>g</u>ac<u>c</u>aagcc<u>t</u>at<u>c</u>tttcattcta<u>c</u><u>a</u>aagat<u>c</u>
ac<u>c</u>tccaagcacgtgaagatgatg<u>c</u>t<u>g</u>ag<u>c</u><u>ggg</u>gtgt<u>g</u>c<u>c</u>t<u>c</u>tt<u>c</u>gctgt<u>c</u>ttcat<u>t</u>g<u>c</u>a<u>c</u>tgctg<u>c</u>c<u>aat</u><u>tc</u>t<u>c</u>gg<u>c</u>
ca<u>cc</u>gg<u>g</u>a<u>tt</u>a<u>c</u>aagat<u>c</u>caggcatc<u>cc</u>gaacctggtg<u>c</u>ttctacaa<u>t</u>a<u>cc</u>gaagacatcaaagat<u>t</u>ggga<u>gg</u>ataggg
tt<u>c</u>ta<u>cc</u>tgct<u>c</u>ctctttagtttcctgggcctgctggct<u>ct</u><u>c</u>ggagtgtc<u>cc</u>tgctgtgtaa<u>c</u>gccatcacagg<u>c</u>atc
ac<u>c</u>ctgctgagagtgaagtttaag<u>tct</u>cagcagca<u>t</u>agacagggcagaa<u>gc</u>cac<u>c</u>a<u>cc</u>tcgagatggt<u>c</u>atccagctg
ctggc<u>c</u>at<u>c</u>atgtg<u>c</u>gtg<u>tct</u>tg<u>c</u>at<u>c</u>tgttgg<u>tct</u>cc<u>c</u>tt<u>c</u>ctggt<u>c</u>acaatggccaacattggga<u>t</u>taat<u>g</u>g<u>t</u>aat
ca<u>c</u>ag<u>c</u>ctggaaacatg<u>c</u>gaaacaacact<u>g</u>tttg<u>cc</u>ct<u>g</u>agaatgg<u>c</u>aa<u>c</u>tggaatcagat<u>tc</u>t<u>g</u>ga<u>cc</u>catggg<u>t</u>g
ta<u>c</u>at<u>cc</u>tgct<u>c</u>agaaaag<u>cc</u>gtgctgaaaatctcta<u>c</u>aagct<u>a</u>gccag<u>c</u>cag<u>t</u>gct<u>g</u>cg<u>gc</u>gtgca<u>c</u>gtgatcagc
<u>c</u>tgca<u>g</u>at<u>c</u>tgggagc<u>t</u>gag<u>c</u>agcat<u>c</u>aagaa<u>c</u>ag<u>cc</u>tgaaggtggc<u>c</u>g<u>cc</u>at<u>c</u>ag<u>c</u>gaga<u>g</u>c<u>cc</u>gtggc<u>c</u>gagaag
ag<u>c</u>g<u>c</u>cagcacct<u>ga</u>

Figure 17

MDSKQQCVKLNDGHFMPVLGFGTYAPPEVPRSKALEVTKLAIEAGFRHIDSAHLYNNEEQVGLA
IRSKIADGSVKREDIFYTSKLWSTFHRPELVRPALENSLKKAQLDYVDLYLIHSPMSLKPGEEL
SPTDENGKVIFDIVDLCTTWEAMEKCKDAGLAKSIGVSNFNRRQLEMILNKPGLKYKPVCNQVE
CHPYFNRSKLLDFCKSKDIVLVAYSALGSQRDKRWVDPNSPVLLEDPVLCALAKKHKRTPALIA
LRYQLQRGVVVLAKSYNEQRIRQNVQVFEFQLTAEDMKAIDGLDRNLHYFNSDSFASHPNYPYS
DEY

Figure 18

```
ATGGATTCCAAACAGCAGTGTGTAAAGCTAAATGATGGCCACTTCATGCCTGTATTGGGATTTGGCACCTATGCACCT
CCAGAGGTTCCGAGAAGTAAAGCTTTGGAGGTCACAAAATTAGCAATAGAAGCTGGGTTCCGCCATATAGATTCTGCT
CATTTATACAATAATGAGGAGCAGGTTGGACTGGCCATCCGAAGCAAGATTGCAGATGGCAGTGTGAAGAGAGAAGAC
ATATTCTACACTTCAAAGCTTTGGTCCACTTTTCATCGACCAGAGTTGGTCCGACCAGCCTTGGAAAACTCACTGAAA
AAAGCTCAATTGGACTATGTTGACCTCTATCTTATTCATTCTCCAATGTCTCTAAAGCCAGGTGAGGAACTTTCACCA
ACAGATGAAAATGGAAAAGTAATATTTGACATAGTGGATCTCTGTACCACCTGGGAGGCCATGGAGAAGTGTAAGGAT
GCAGGATTGGCCAAGTCCATTGGGGTGTCAAACTTCAACCGCAGGCAGCTGGAGATGATCCTCAACAAGCCAGGACTC
AAGTACAAGCCTGTCTGCAACCAGGTAGAATGTCATCCGTATTTCAACCGGAGTAAATTGCTAGATTTCTGCAAGTCG
AAAGATATTGTTCTGGTTGCCTATAGTGCTCTGGGATCTCAACGAGACAAACGATGGGTGGACCCGAACTCCCCGGTG
CTCTTGGAGGACCCAGTCCTTTGTGCCTTGGCAAAAAAGCACAAGCGAACCCCAGCCCTGATTGCCCTGCGCTACCAG
CTGCAGCGTGGGGTTGTGGTCCTGGCCAAGAGCTACAATGAGCAGCGCATCAGACAGAACGTGCAGGTTTTTGAGTTC
CAGTTGACTGCAGAGGACATGAAAGCCATAGATGGCCTAGACAGAAATCTCCACTATTTTAACAGTGATAGTTTTGCT
AGCCACCCTAATTATCCATATTCAGATGAATATTAA
```

TREATING GLAUCOMA, CARDIOVASCULAR DISEASES, AND RENAL DISEASES

CROSS-REFERENCE TO RELATED APPLICATIONS

This application is a continuation of U.S. Ser. No. 15/187,471, filed Jun. 20, 2016 (now U.S. Pat. No. 10,058,597), which is a continuation of U.S. Ser. No. 14/510,921, filed Oct. 9, 2014 (now U.S. Pat. No. 9,393,322), which is a continuation of U.S. Ser. No. 13/624,383, filed Sep. 21, 2012 (now U.S. Pat. No. 8,871,733), which is a continuation application of U.S. Ser. No. 12/298,431, filed Aug. 6, 2009 (now U.S. Pat. No. 8,299,043), which is a National Stage application under 35 U.S.C. § 371 and claims benefit of International Application No. PCT/US2007/067710 having an International Filing Date of Apr. 27, 2007, which claims the benefit of priority of U.S. Provisional Application No. 60/795,789 having a filing date of Apr. 28, 2006. The disclosures of the prior applications are considered part of (and are incorporated by reference in) the disclosure of this application.

STATEMENT AS TO FEDERALLY SPONSORED RESEARCH

This invention was made with government support under EY014411 awarded by the National Institutes of Health. The government has certain rights in the invention.

BACKGROUND

1. Technical Field

This document relates to methods and materials involved in treating glaucoma, cardiovascular diseases, and renal diseases. For example, this document relates to methods and materials that can be used to reduce intraocular pressure.

2. Background Information

Glaucoma is characterized by a loss of visual function due to damage to the optic nerve. The several morphologically or functionally distinct types of glaucoma are typically characterized by elevated intraocular pressure, which is considered to be causally related to the pathological course of the disease. Ocular hypertension is a condition where intraocular pressure is elevated but no apparent loss of visual function has occurred. Such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility.

SUMMARY

This document provides methods and materials related to treating glaucoma, ocular hypertension, cardiovascular diseases, and renal diseases. For example, this document provides isolated nucleic acid molecules encoding a polypeptide having COX-2 activity as well as isolated nucleic acid molecules encoding a polypeptide having prostaglandin $F_{2\alpha}$ receptor activity. In addition, this document provides viral vectors (e.g., lentiviral vectors) containing nucleic acid encoding a polypeptide having COX-2 activity, a polypeptide having prostaglandin $F_{2\alpha}$ receptor activity, a polypeptide having prostacyclin IP receptor activity, a polypeptide having prostaglandin synthase activity, a polypeptide having prostacyclin synthase activity, or combinations thereof. Such isolated nucleic acid molecules and viral vectors can be used to reduce intraocular pressure and to treat cardiovascular and renal diseases. For example, viral vectors provided herein can be administered to the eye or eyes of a human patient having elevated intraocular pressure, thereby reducing the patient's risk of developing glaucoma. Viral vectors provided herein also can be administered to the heart of a human patient having cardiovascular disease, thereby reducing the patient's risk of having a myocardial infarction. In some cases, viral vectors provided herein can be administered to the kidneys of a human patient having renal disease, thereby reducing the patient's risk of having renal failure.

This document also provides methods and materials for reducing intraocular pressure. For example, the methods provided herein can include administering a viral vector such as a lentiviral vector to one or both eyes. Such methods can be used to treat existing glaucoma or can be used to slow or prevent the onset of glaucoma. In some cases, the methods and materials provided herein can be used to reduce a human patient's risk of developing glaucoma. In some cases, the methods and materials provided herein can be used to increase a mammal's ability to respond to an intraocular pressure reducing treatment such as Latanoprost (xalatan) eye drops.

This document also provides methods and materials for treating cardiovascular and renal diseases. For example, the methods provided herein can include administering a viral vector systemically, administering a viral vector to the heart (e.g., via a catheter), or administering a viral vector to one or both kidneys (e.g., via a urethral catheter or during dialysis). Such methods can be used to reduce the severity of a symptom of a cardiovascular or renal disease (e.g., hypertension or renal fibrosis) and can be used to reduce the progression of a cardiovascular or renal disease (e.g., to reduce progressive loss of function of the heart or kidneys).

In general, one aspect of this document features a method for treating a mammal having glaucoma or elevated intraocular pressure. The method comprises, or consists essentially of, administering a nucleic acid to an eye of the mammal under conditions effective to reduce intraocular pressure of the eye, wherein the nucleic acid comprises a nucleic acid sequence encoding a polypeptide having cyclooxygenase-2 activity and a nucleic acid sequence encoding a polypeptide having prostaglandin $F_{2\alpha}$ receptor activity. The nucleic acid can be administered to said eye using a viral vector (e.g., a lentiviral vector).

In another aspect of this document features a method for treating a mammal having glaucoma or elevated intraocular pressure. The method comprises, or consists essentially of, administering a viral vector to an eye of the mammal under conditions effective to reduce intraocular pressure of the eye, where the viral vector comprises a nucleic acid encoding a polypeptide having cyclooxygenase-2 activity. The mammal can be a human. The viral vector can be a lentiviral vector. The administering step can comprise contacting the eye with a solution containing the viral vector. The solution can be a saline solution or a physiologically acceptable buffered solution. The solution can comprise between $10^3$ and $10^{12}$ lentivirus particles per mL (e.g., between $10^4$ and $10^{11}$ lentivirus particles per mL; between $10^5$ and $10^{10}$ lentivirus particles per mL; between $10^6$ and $10^{10}$ lentivirus particles per mL; or between $10^6$ and $10^9$ lentivirus particles per mL). The nucleic acid can be a template for an mRNA molecule encoding the polypeptide, where the mRNA has an increased stability in cells as compared to the stability of an mRNA molecule transcribed from the sequence set forth in SEQ ID NO:2. The nucleic acid can comprise a nucleic acid sequence that encodes the same amino acid sequence as set forth in SEQ ID NO:1 and can comprise a codon sequence different than the codons set forth in SEQ ID NO:2. The nucleic acid sequence can comprise five or more different codon sequences compared to the codon sequences set forth in SEQ ID NO:2. The nucleic acid can comprise the sequence set forth in SEQ ID NO:3. The polypeptide can comprise the sequence set forth in SEQ ID NO:1. The viral vector can comprise a nucleic acid sequence encoding a polypeptide having prostaglandin $F_{2\alpha}$ receptor activity. The nucleic acid sequence encoding the polypeptide having prostaglandin $F_{2\alpha}$ receptor activity can be a template for an mRNA molecule encoding the polypeptide having prostaglandin $F_{2\alpha}$ receptor activity, where the mRNA has an increased stability in cells as compared to the stability of an mRNA molecule transcribed from the sequence set forth in SEQ ID NO:5. The nucleic acid sequence encoding the polypeptide having prostaglandin $F_{2\alpha}$ receptor activity can comprise a nucleic acid sequence that encodes the same amino acid sequence as set forth in SEQ ID NO:4 and can comprise a codon sequence different than the codons set forth in SEQ ID NO:5. The nucleic acid sequence encoding the polypeptide having prostaglandin $F_{2\alpha}$ receptor activity can comprise five or more different codon sequences compared to the codon sequences set forth in SEQ ID NO:5. The nucleic acid sequence encoding the polypeptide having prostaglandin $F_{2\alpha}$ receptor activity can comprise the sequence set forth in SEQ ID NO:6. The polypeptide having prostaglandin $F_{2\alpha}$ receptor activity can comprise the sequence set forth in SEQ ID NO:4. The viral vector can comprise a nucleic acid sequence encoding a polypeptide having prostaglandin synthase activity. The nucleic acid sequence encoding the polypeptide having prostaglandin synthase activity can comprise the sequence set forth in SEQ ID NO:8. The polypeptide having prostaglandin synthase activity can comprise the sequence set forth in SEQ ID NO:7. The viral vector can comprise nucleic acid encoding a polypeptide having prostaglandin $F_{2\alpha}$ receptor activity and a polypeptide having prostaglandin synthase activity. The method can be effective to reduce the intraocular pressure by at least 10 percent. The method can be effective to reduce the intraocular pressure by at least 20 percent. The method can be effective to reduce the intraocular pressure by at least 30 percent. The viral vector can be a feline immunodeficiency virus vector.

In another aspect, this document features a method for treating a mammal having a cardiovascular or renal disease. The method comprises, or consists essentially of, administering a viral vector to the mammal under conditions effective to reduce the severity of a symptom of the cardiovascular or renal disease, where the viral vector comprises a nucleic acid encoding a polypeptide having cyclooxygenase-2 activity. The mammal can be a human. The viral vector can be a lentiviral vector. The nucleic acid can be a template for an mRNA molecule encoding the polypeptide, where the mRNA has an increased stability in cells as compared to the stability of an mRNA molecule transcribed from the sequence set forth in SEQ ID NO:2. The nucleic acid can comprise a nucleic acid sequence that encodes the same amino acid sequence as set forth in SEQ ID NO:1 and can comprise a codon sequence different than the codons set forth in SEQ ID NO:2. The nucleic acid sequence can comprise five or more different codon sequences compared to the codon sequences set forth in SEQ ID NO:2. The nucleic acid can comprise the sequence set forth in SEQ ID NO:3. The polypeptide can comprise the sequence set forth in SEQ ID NO:1. The viral vector can comprise a nucleic acid sequence encoding a polypeptide having prostacyclin IP receptor activity. The nucleic acid can comprise a nucleic acid sequence that encodes the same amino acid sequence as set forth in SEQ ID NO:9 and can comprise a codon sequence different than the codons set forth in SEQ ID NO:10. The nucleic acid sequence encoding the polypeptide having prostacyclin IP receptor activity can comprise the sequence set forth in SEQ ID NO:10. The polypeptide having prostacyclin IP receptor activity can comprise the sequence set forth in SEQ ID NO:9. The viral vector can comprise a nucleic acid sequence encoding a polypeptide having prostacyclin synthase activity. The nucleic acid sequence encoding the polypeptide having prostacyclin synthase activity can comprise the sequence set forth in SEQ ID NO:12. The polypeptide having prostacyclin synthase activity can comprise the sequence set forth in SEQ ID NO:11. The viral vector can comprise nucleic acid encoding two or more polypeptides selected from the group consisting of a polypeptide having cyclooxygenase-2 activity, a polypeptide having prostacyclin IP receptor activity, and a polypeptide having prostacyclin synthase activity. The symptom can be reduced by 25%. The symptom can be reduced by 50%. The symptom can be reduced by 75%. The symptom can be reduced by 100%.

In another aspect, this document features a viral vector comprising a nucleic acid encoding a polypeptide having cyclooxygenase-2 activity. The viral vector can be a lentiviral vector. The nucleic acid can be a template for an mRNA molecule encoding the polypeptide, where the mRNA has an increased stability in cells as compared to the stability of an mRNA molecule transcribed from the sequence set forth in SEQ ID NO:2. The nucleic acid can comprise a nucleic acid sequence that encodes the same amino acid sequence as set forth in SEQ ID NO:1 and can comprise a codon sequence different than the codons set forth in SEQ ID NO:2. The nucleic acid sequence can comprise five or more different codon sequences compared to the codon sequences set forth in SEQ ID NO:2. The nucleic acid can comprise the sequence set forth in SEQ ID NO:3. The polypeptide can comprise the sequence set forth in SEQ ID NO:1. The viral vector can comprise a nucleic acid sequence encoding a polypeptide having prostaglandin $F_{2\alpha}$ receptor activity. The nucleic acid sequence encoding the polypeptide having prostaglandin $F_{2\alpha}$ receptor activity can be a template for an mRNA molecule encoding the polypeptide having prostaglandin $F_{2\alpha}$ receptor activity, where the mRNA has an increased stability in cells as compared to the stability of an mRNA molecule transcribed from the sequence set forth in SEQ ID NO:5. The nucleic acid sequence encoding the polypeptide having prostaglandin $F_{2\alpha}$ receptor activity can comprise a nucleic acid sequence that encodes the same amino acid sequence as set forth in SEQ ID NO:4 and can comprise a codon sequence different than the codons set forth in SEQ ID NO:5. The nucleic acid sequence encoding the polypeptide having prostaglandin $F_{2\alpha}$ receptor activity can comprise five or more different codon sequences compared to the codon sequences set forth in SEQ ID NO:5. The nucleic acid sequence encoding the polypeptide having prostaglandin $F_{2\alpha}$ receptor activity can comprise the sequence set forth in SEQ ID NO:6. The polypeptide having prostaglandin $F_{2\alpha}$ receptor activity can comprise the sequence set forth in SEQ ID NO:4. The viral vector can comprise a nucleic acid sequence encoding a polypeptide having prostaglandin synthase activity. The nucleic acid sequence encoding the polypeptide having prostaglandin synthase activity can comprise the sequence set forth in SEQ ID NO:8. The polypeptide having prostaglandin synthase activity can comprise the sequence set forth in SEQ ID NO:7. The viral vector can comprise nucleic acid encoding a polypeptide having prostaglandin $F_{2\alpha}$ receptor activity and a polypeptide having prostaglandin synthase activity. The viral vector can comprise nucleic acid encoding a polypeptide having prostacyclin IP receptor activity. The nucleic acid can comprise a nucleic acid sequence that encodes the same amino acid sequence as set forth in SEQ ID NO:9 and can comprise a codon sequence different than the codons set forth in SEQ ID NO:10. The nucleic acid sequence encoding the polypeptide having prostacyclin IP receptor activity can comprise the sequence set forth in SEQ ID NO:10. The polypeptide having prostacyclin IP receptor activity can comprise the sequence set forth in SEQ ID NO:9. The viral vector can comprise a nucleic acid sequence encoding a polypeptide having prostacyclin synthase activity. The nucleic acid sequence encoding the polypeptide having prostacyclin synthase activity can comprise the sequence set forth in SEQ ID NO:12. The polypeptide having prostacyclin synthase activity can comprise the sequence set forth in SEQ ID NO:11. The viral vector can comprise nucleic acid encoding two or more polypeptides selected from the group consisting of a polypeptide having cyclooxygenase-2 activity, a polypeptide having prostacyclin IP receptor activity, and a polypeptide having prostacyclin synthase activity.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 is a Northern blot analyzing expression of COX-2 mRNA in cells transfected with a transfer construct containing the codon-optimized (XOGWF) or wild-type (COX2igWF) COX-2 cDNA. Cells transfected with a transfer construct containing a GFP coding sequence operably linked to a CMV promoter (GINWF) served as a positive control, and mock transfected cells served as a negative control.

FIG. 7 also contains Western blots analyzing expression of COX-2 and PGFS polypeptides in the transfected 293T cells.

FIG. 8 is a chart indicating the therapeutic regimen applied to each subject in the animal study.

FIG. 11 is a listing of an amino acid sequence (SEQ ID NO:1) of a human COX-2 polypeptide.

FIG. 12 is a listing of a wild-type human nucleic acid sequence (SEQ ID NO:2) encoding the amino acid sequence set forth in SEQ ID NO:1.

FIG. 13 is a listing of a codon optimized nucleic acid sequence (SEQ ID NO:3) encoding the amino acid sequence set forth in SEQ ID NO:1. The bold, underlined nucleotides represent nucleotides that were changed relative to the sequence set forth in SEQ ID NO:2.

FIG. 14 is a listing of an amino acid sequence (SEQ ID NO:4) of a human prostaglandin $F_{2\alpha}$ receptor polypeptide containing an HA tag. The underlined amino acid sequence represents the HA tag.

FIG. 15 is a listing of a wild-type human nucleic acid sequence (SEQ ID NO:5) encoding the amino acid sequence set forth in SEQ ID NO:4.

FIG. 16 is a listing of a codon optimized nucleic acid sequence (SEQ ID NO:6) encoding the amino acid sequence set forth in SEQ ID NO:4. The bold, underlined nucleotides represent nucleotides that were changed relative to the sequence set forth in SEQ ID NO:5.

FIG. 17 is a listing of an amino acid sequence (SEQ ID NO:7) of a human prostaglandin F synthase polypeptide.

FIG. 18 is a listing of a nucleic acid sequence (SEQ ID NO:8) encoding a human prostaglandin F synthase polypeptide.

DETAILED DESCRIPTION

Figure 1:
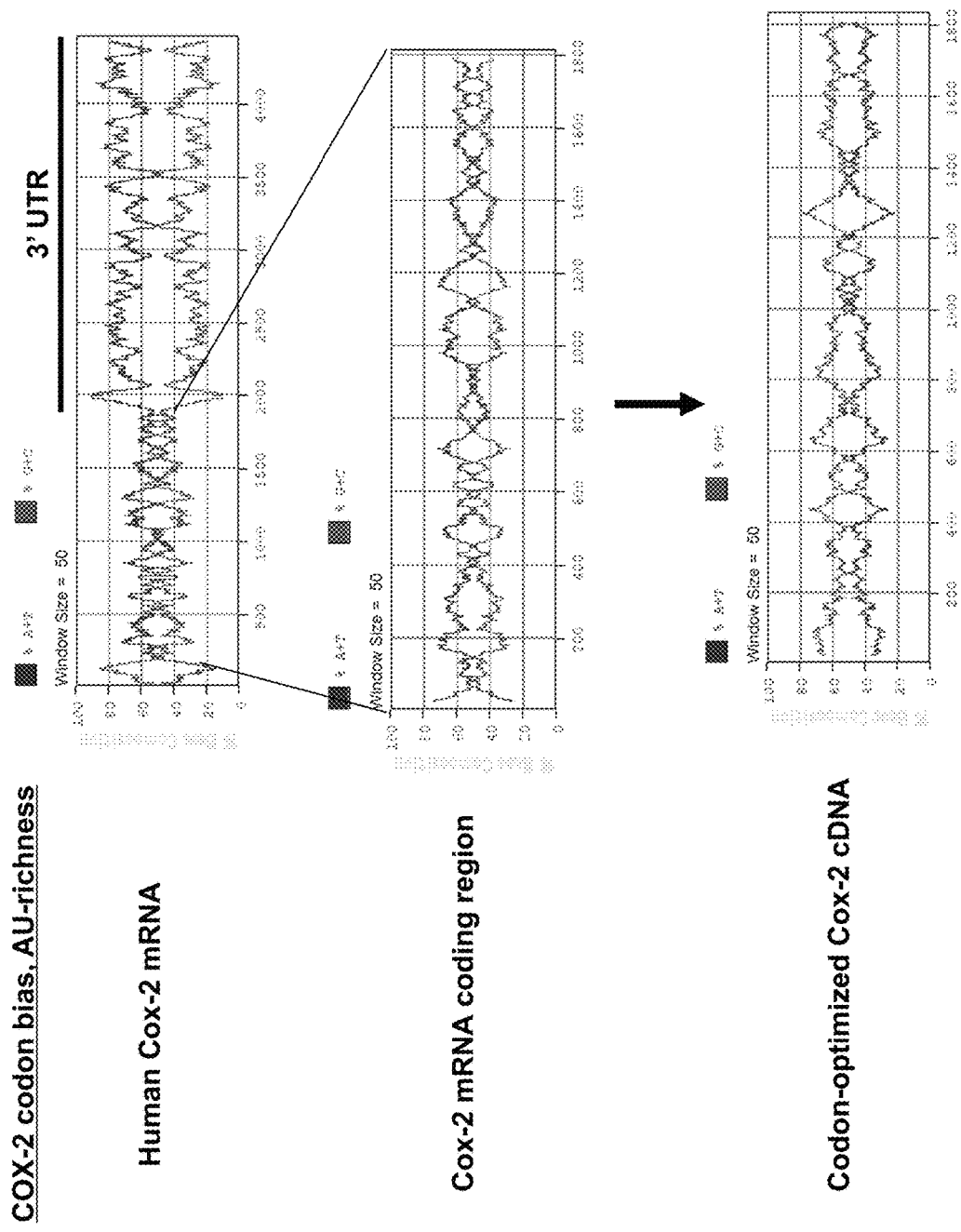
FIG. 1 contains graphs plotting the percent base composition versus base position in the human COX-2 mRNA (Upper panel), the coding region of the human COX-2 mRNA (middle panel), and the codon-optimized COX-2 cDNA (lower panel).

This document provides methods and materials related to treating glaucoma, intraocular hypertension, cardiovascular disease, and renal disease. For example, this document provides isolated nucleic acid molecules encoding a polypeptide having COX-2 activity as well as isolated nucleic acid molecules encoding a polypeptide having prostaglandin $F_{2\alpha}$ receptor activity. This document also provides viral vectors (e.g., lentiviral vectors) containing a polypeptide having COX-2 activity, a polypeptide having prostaglandin $F_{2\alpha}$ receptor activity, a polypeptide having prostacyclin IP receptor activity, a polypeptide having prostaglandin synthase activity, a polypeptide having prostacyclin synthase activity, or combinations thereof.

In addition, this document provides methods and materials for reducing intraocular pressure. For example, the methods provided herein can include administering a viral vector such as a lentiviral vector to one or both eyes. Such methods can be used to treat existing glaucoma or can be used to slow or prevent the onset of glaucoma. In some cases, the methods and materials provided herein can be used to reduce a human patient's risk of developing glaucoma.

This document also provides methods and materials for treating cardiovascular diseases (e.g., pulmonary hypertension) and renal diseases (e.g., diabetic nephropathy). For example, the methods provided herein can include administering a viral vector systemically, administering a viral vector to the heart, or administering a viral vector to one or both kidneys. Such methods can be used to reduce the severity of a symptom of a cardiovascular or renal disease (e.g., hypertension or renal fibrosis) and can be used to reduce the progression of a cardiovascular or renal disease (e.g., to reduce progressive loss of function of the heart or kidneys).

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

An isolated nucleic acid molecule provided herein can contain a nucleic acid sequence encoding a polypeptide having COX-2 activity, a polypeptide having prostaglandin $F_{2\alpha}$ receptor activity, a polypeptide having prostacyclin IP receptor activity, a polypeptide having prostaglandin synthase activity, a polypeptide having prostacyclin synthase activity, or combinations thereof. Non-limiting examples of nucleic acid sequences encoding a polypeptide having COX-2 activity, a polypeptide having prostaglandin $F_{2\alpha}$ receptor activity, a polypeptide having prostacyclin IP receptor activity, a polypeptide having prostaglandin synthase activity, and a polypeptide having prostacyclin synthase activity are set forth in SEQ ID NO:2, SEQ ID NO:5, SEQ ID NO:10 (GenBank® GI Number GI:39995095), SEQ ID NO:8, and SEQ ID NO:12 (GenBank® GI Number GI:75517290), respectively. Non-limiting examples of amino acid sequences of polypeptides having COX-2 activity, prostaglandin $F_{2\alpha}$ receptor activity, prostacyclin IP receptor activity, prostaglandin synthase activity, and prostacyclin synthase activity are set forth in SEQ ID NO:1, SEQ ID NO:4, SEQ ID NO:9 (GenBank® GI Number GI:4506263), SEQ ID NO:7, and SEQ ID NO:11 (GenBank® GI Number GI:2493373), respectively.

Isolated nucleic acid molecules provided herein can contain a sequence that has one or more codons that are different from those found in a wild-type sequence. For example, an isolated nucleic acid molecule provided herein can contain a nucleic acid sequence that encodes a polypeptide having COX-2 activity that is identical to a human COX-2 polypeptide with the nucleic acid sequence having one or more codons that are different from wild-type human nucleic acid encoding that human COX-2 polypeptide. An example of such a nucleic acid molecule is provided in FIG. 13.

Any method can be used to obtain an isolated nucleic acid molecule provided herein including, without limitation, common molecular cloning and chemical nucleic acid synthesis techniques. For example, PCR can be used to obtain an isolated nucleic acid molecule containing a nucleic acid sequence set forth in FIG. 12. In some cases, the obtained nucleic acid can be mutated to form a codon-optimized sequence such as the sequence set forth in FIG. 13.

Any of the nucleic acid molecules provided herein can be incorporated into a viral vector. For example, a viral vector can be designed to contain an isolated nucleic acid molecule having a nucleic acid sequence encoding a polypeptide having COX-2 activity, a polypeptide having prostaglandin $F_{2\alpha}$ receptor activity, a polypeptide having prostacyclin IP receptor activity, a polypeptide having prostaglandin synthase activity, a polypeptide having prostacyclin synthase activity, or combinations thereof. Examples of viral vectors that can be used include, without limitation, lentiviral vectors (e.g., feline immunodeficiency viral vectors), retroviral vectors (e.g., murine retroviral vectors), foamy virus vectors, adenovirus vectors, adeno-associated virus vectors, vaccinia virus vectors, and herpes virus vectors. Viral vectors can be replication incompetent and can contain few if any viral genes. In some cases, the isolated nucleic acid molecules provided herein can used as naked DNA or can be incorporated into plasmids, transposons, retroelement-based vectors, or phage integrase containing DNA vectors.

This document provides methods for treating glaucoma or intraocular hypertension. Such methods can include administering an isolated nucleic acid molecule provided herein to a mammal in need of treatment (e.g., a human, dog, cat, horse, cow, pig, or monkey). Any method can be used to administer an isolated nucleic acid molecule provided herein. For example, a viral vector provided herein can be administered to a mammal via oral administration or direct administration to one or both eyes. In some cases, a viral vector provided herein can be contained within a solution that can be directly applied to an eye. Any method can be used to administer such a solution to an eye. For example, a solution containing a viral vector provided herein can be administered in a manner similar to the manner used to self administer eye drops.

As described herein, this document provides methods and materials for treating cardiovascular and renal diseases. Cardiovascular diseases include, without limitation, pulmonary hypertension (e.g., pulmonary arteriolar hypertension), arterial thrombosis, myocardial ischemia, myocardial infarction, atherosclerosis, restenosis, and reperfusion injury. Examples of renal diseases include, without limitation, diabetic nephropathy, progressive renal disease, renal fibrosis, renal hypertrophy, and glomerulosclerosis. As described herein, a mammal having a cardiovascular or renal disease can be treated using an isolated nucleic acid molecule provided herein (e.g., an isolated nucleic acid molecule encoding a polypeptide having cyclooxygenase-2 activity, a polypeptide having prostacyclin IP receptor activity, a polypeptide having prostacyclin synthase activity, or any combination thereof). A viral vector containing an isolated nucleic acid molecule provided herein can be used to administer the nucleic acid to a mammal in need of treatment. Viral vectors can be prepared using standard materials (e.g., packaging cell lines and vectors) and methods known to those of ordinary skill in the art.

Viral vectors containing one or more nucleic acid molecules provided herein (e.g., one or more of a nucleic acid encoding a polypeptide having cyclooxygenase-2 activity, a nucleic acid encoding a polypeptide having prostacyclin IP receptor activity, and a nucleic acid encoding a polypeptide having prostacyclin synthase activity) can be administered to a mammal having a cardiovascular or renal disease via numerous routes. For example, a viral vector can be administered systemically (e.g., via intravenous injection). In some cases, a viral vector can be administered directly to the heart. Direct administration of a viral vector to the heart can be achieved using a catheter or a stent, for example, and can be performed during a therapeutic manipulation such as arterial bypass surgery. In some cases, a viral vector can be administered directly to one or both kidneys. Various methods can be used to deliver a viral vector to a kidney. For example, a urethral catheter can be used to deliver a viral vector to a kidney. In some cases, a viral vector can be delivered to a kidney during dialysis or by direct injection into the kidney (e.g., CT-guided direct needle injection into the kidney). In some cases, a viral vector can be targeted to the heart or kidneys using liposomes or by expressing a polypeptide on the surface of the viral particle that interacts with another polypeptide that is expressed predominantly or selectively on the surface of heart or kidney cells. In some cases, one or more nucleic acid molecules provided herein can be administered to a mammal having cardiovascular or renal disease by direct injection of the naked nucleic acid molecules into the heart or kidney, or by direct administration of liposomes containing the nucleic acid molecules. As with viral vectors, liposomes also can be targeted to heart or kidney tissue. Viral vectors, naked nucleic acids, and liposomes can be administered to a mammal in a biologically compatible solution or a pharmaceutically acceptable delivery vehicle. Suitable pharmaceutical formulations depend in part on the use and route of delivery. For example, a suitable formulation for direct injection is isotonic and has a neutral pH.

After identifying a mammal as having glaucoma, intraocular hypertension, a cardiovascular disease, or a renal disease, the mammal can be administered a viral vector containing a nucleic acid disclosed herein. A viral vector can be administered to a mammal in any amount, at any frequency, and for any duration effective to achieve a desired outcome (e.g., to reduce the severity of a symptom of glaucoma, cardiovascular disease, or renal disease). In some cases, a viral vector can be administered to a mammal having glaucoma, intraocular hypertension, a cardiovascular disease, or a renal disease to reduce the severity of a symptom or to reduce the progression rate of the condition by 5, 10, 25, 50, 75, 100, or more percent. For example, the severity of a symptom can be reduced in a mammal such that the symptom is no longer detected by the mammal. In some cases, the progression of a condition can be reduced such that no additional progression is detected. Any method can be used to determine whether or not the severity of a symptom or the progression rate of a condition is reduced. For example, a mammal having glaucoma can be tested for intraocular pressure before and after treatment to determine whether the pressure is reduced. In some cases, a mammal can be observed or tested for the severity of a symptom of cardiovascular disease (e.g., high blood pressure, blood clots in arteries and veins, pain isolated to one leg (usually the calf or medial thigh), swelling in the extremity, or varicose veins) before and after treatment to determine whether or not the severity of a symptom is reduced. In some cases, renal biopsy tissue taken from a mammal before and after treatment can be analyzed (e.g., for fibrosis) to determine whether the severity of a symptom is reduced. To determine whether or not progression of a condition (e.g., glaucoma, intraocular hypertension, cardiovascular disease, or renal disease) is reduced, a physical examination can be performed at different time points to determine the stage or severity of the condition. The stage or severity of the condition observed at different time points can be compared to assess the progression rate. After treatment as described herein, the progression rate can be determined again over another time interval to determine whether or not the progression rate has decreased. For example, renal function can be assessed at various time points to determine whether the function is improving, worsening, or staying the same.

An effective amount of a viral vector can be any amount that reduces the severity of a symptom or the progression of a condition (e.g., glaucoma, intraocular hypertension, cardiovascular disease, or renal disease) without producing significant toxicity to the mammal. If a particular mammal fails to respond to a particular amount, then the amount of the viral vector can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, immunocompetency of the mammal, and severity of the condition may require an increase or decrease in the actual effective amount administered.

The frequency of administration can be any frequency that reduces the severity of a symptom or progression rate of a condition without producing significant toxicity to the mammal. For example, the frequency of administration can be from about once in a lifetime to about once a month. The frequency of administration can remain constant or can be variable during the duration of treatment. A course of treatment with a viral vector can include rest periods. For example, a viral vector can be administered over a six month period followed by a three month rest period, and such a regimen can be repeated multiple times. As with the effective amount, various factors can influence the actual frequency of administration used for a particular application. For example, the effective amount, duration of treatment, use of multiple treatment agents, route of administration, immunocompetency of the mammal, and severity of the condition may require an increase or decrease in administration frequency.

An effective duration for administering a viral vector provided herein can be any duration that reduces the severity of a symptom or the progression rate of glaucoma, intraocular hypertension, cardiovascular disease, or renal disease without producing significant toxicity to the mammal. Thus, the effective duration can vary from several days to several weeks, months, or years. In general, the effective duration for the treatment of glaucoma, intraocular hypertension, cardiovascular disease, or renal disease can range in duration from several months to several years. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, immunocompetency of the mammal, and severity of the condition.

The invention will be further described in the following examples, which do not limit the scope of the invention described in the claims.

EXAMPLES

Example 1—Modulation of Prostaglandin Pathways Reduces Intraocular Pressure

Experiments were conducted to determine whether expression of polypeptides involved in prostaglandin biosynthetic and response pathways can be manipulated to provide a sustained improvement in intraocular pressure involved in diseases such as glaucoma.

Methods and Materials

Cloning FIV-Based Transfer Construct Plasmids pCOX2igWF: A plasmid having the normal human COX-2 cDNA (obtained from S. Prescott, Huntsman Cancer Institute) was NotI-XbaI-digested to isolate the COX-2 cDNA and blunted with T4 polymerase. pGiNWF (Loewen et al., *Investig. Ophthalmol. Vis. Sci.*, 43:3686-3690 (2002)) was digested with AgeI and EcoRI, and blunted with T4 polymerase to isolate the backbone sequence that was then ligated with the COX-2 cDNA insert. Next, an IRES (internal ribosome entry site)-GFP cassette was blunt-end ligated into the EcoRI site just downstream of COX-2. This insertion resulted in a bicistronic FIV-based transfer construct with COX-2 expression driven by the CMV promoter and GFP expression being driven by the IRES just downstream of the COX-2 cDNA cassette. This plasmid, COX2igWF, was the basis for the cloning of the following transfer constructs.

pXOGWF: A codon-optimized human COX-2 cDNA was designed and synthesized with the assistance of GenScript Corporation custom services (Scotch Plains, N.J.). Codon usage was optimized for usage in mammalian cells. G-C content was optimized, and other factors such as secondary structure and repetitive codons were taken into consideration to achieve codon optimization. The codon-optimized COX-2 cDNA was designed to include flanking restriction sites to enable downstream recombinant cloning strategies. BamHI sites flank the codon-optimized COX-2 gene, and these sites were used to insert the optimized cDNA into the BamHI-digested backbone of COX2igWF. This essentially replaced the wild-type COX-2 cDNA cassette with the codon-optimized COX-2 cDNA.

pGFSigWF: The PGFS cDNA from hPGFS-cDNA pUC8 (obtained from Kikuko Watanabe, University of East Asia, Japan) was removed by EcoRI and SalI digestion, and blunted with T4 DNA polymerase. This cDNA insert was blunt ligated into the BamHI-digested backbone of COX2igWF.

pHAFPRigWF: An HA-tagged prostaglandin F receptor (HAFPR) cDNA plasmid (obtained from G. FitzGerald, University of Pennsylvania, USA), HA-FP, contains the HAFPR cDNA flanked by an upstream KpnI and a downstream NcoI site. The HAFPR cassette was removed by KpnI-NcoI digestion, blunted with T4 DNA polymerase and ligated with T4 DNA ligase into the BamHI-digested backbone of COX2igWF.

pcoFPRigWF: A codon-optimized human HA-tagged FPR cDNA was designed and synthesized with the assistance of GenScript Corporation custom services (Scotch Plains, N.J.). Codon usage was optimized for usage in mammalian cells. G-C content was optimized, and other factors such as secondary structure and repetitive codons were taken into consideration to achieve codon optimization. The codon-optimized HAFPR was designed to include flanking restriction sites for accessible cloning strategies. BamHI sites flank the codon-optimized HAFPR gene and were used to digest and ligate into the BamHI-digested backbone of COX2igWF.

PGF2alpha Assay 293T cells in 6 well plates were transfected with 2 μg XOGWF or PGFSigWF using the calcium phosphate transfection method as described elsewhere (Loewen et al.,

*Methods Mol. Biol.*, 229:251-271 (2003)). Media was changed 12 to 16 hours later and collected 24 hours thereafter. Media was filtered (0.2 µm) to remove cells and used in the Prostaglandin F2 α enzyme immunoassay kit (Cayman Chemical, cat. no. 516011) as recommended by the manufacturer's protocol manual.

Northern Blot 293T cells were transfected with equivalent quantities of COX2igWF, XOWGF, or GINWF. Cells were treated with 1 mL Trizol 36 hours post-transfection and stored at −80° C. until RNA purification. Trizol-treated lysates were treated with chloroform, followed by isopropanol, and spun to isolate nucleic acid. Nucleic acid was treated with DNase, followed by RNA extraction with equal volume of phenol:chloroform:isoamyl alcohol (125:24:1). RNA was precipitated with 1/10 volume 3M sodium acetate and 2.5 volumes 100% ethanol.

Isolated total cellular RNA was separated by gel electrophoresis (1.2% agarose gel, 3.75% formaldehyde, 1×MOPS). After gel electrophoresis, RNA was transferred onto a nylon transfer membrane (Nytran Supercharge Membrane, Schleicher & Schuell, cat. no. 10416284).

A beta-actin anti-sense oligo probe was 5'-end labeled using T4 PNK (Promega) and [$\gamma$-$^{32}$P]ATP incubated at 37° C. for 30 minutes followed by heat inactivation at 70° C. for 10 minutes. Labeled primer probe was purified using a quick spin column and hybridized with RNA on nylon membrane overnight at 42° C. The membrane was washed and then exposed to MR X-ray film (Kodak) at −80° C. for five days and developed.

Since all transfer constructs contain the GFP gene cassette to be included in the message, mRNA expression levels for each message were assessed by probing for GFP sequence common to all messages in this experiment.

25 ng of GFP anti-sense oligo probe was randomly labeled using dNTP stock solution, 50 µCi α-dCTP and Klenow. The random labeling reaction occurred at 37° C. for 1 hour and was heat-inactivated at 65° C. for 10 minutes. Random labeled probe was purified using a quick spin column followed by hybridization with the RNA-containing nylon membrane for 5 hours to 3 days at −80° C. The membrane was exposed to MR X-ray film (Kodak) and developed.

Western Blot

For Western blotting, cells were lysed in Tris-buffered saline containing 1% Triton X-100 and 1% NP-40, plus a protease inhibitor cocktail (Complete-mini; Boehringer). Lysates were centrifuged to remove chromatin. Proteins were resolved in sodium dodecyl sulfate-10% polyacrylamide gels and transferred to Immobilon P membranes (Millipore). Blocked membranes were incubated overnight at 4° C. or for 2 hours at room temperature with mouse anti-COX-2 MAb (Cayman Chemical, cat. no. 160112), rat anti-HA MAb (Roche), or rabbit anti-hPGFS Ab (obtained from Kikuko Watanabe), diluted in Tris-buffered saline-5% nonfat milk plus 0.05% Tween 20. After washing, membranes were incubated with the appropriate horseradish peroxidase-tagged secondary antibody. Bound antibodies were detected by ECL (Amersham Pharmacia Biotech).

Vector Production and Titration

Transfections were performed using the calcium phosphate transient transfection method in ten-chamber cell factories (CF10) as described elsewhere (Loewen et al., *Methods Mol. Biol.*, 229:251-271 (2003)). Medium was changed 12 to 16 hours later, and supernatants were collected 48 hours thereafter, filtered through a 0.2-µm-pore-size filter, and concentrated by two rounds of ultracentrifugation. The first spin was performed in a series of 250 mL polyallomer Oakridge ultracentrifuge bottles (Sorvall, cat. no. 54477) at 19,000 rpm in a SureSpin 630 rotor (Sorvall, cat. no. 79367) in a Sorvall Discovery 100SE ultracentrifuge (67,000 $g_{rmax}$) for 6 hours at 4° C. Supernatant was removed, and vector was resuspended in 30 mL PBS and centrifuged over a sucrose cushion in a swinging bucket SW41TI rotor at 24,000 rpm for 2 hours at 4° C., and aliquoted and frozen at −80° C.

CrFK cells were transduced with serial dilutions of each vector preparation. 48 hours after transduction, cells were harvested, and titers of each vector preparation were determined by flow cytometry for GFP expression. All preparations were tested for reverse transcriptase (RT) activity as described elsewhere (Saenz et al., *J. Virol.*, 79(24):15175-88 (2005)).

Vector Administration to Cat Anterior Chamber

Experiments were conducted in pathogen-free domestic cats (Harlan, Indianapolis, Ind.). Prior to vector administration, cats were anesthetized with 10 mg/kg intramuscular tiletamine HCl/zolazepam HCl (Telazol; Fort Dodge Laboratories Inc., Fort Dodge, Iowa) injection. Anterior chambers of feline eyes were transcorneally injected with a bolus of 200 µL PBS containing $10^7$ TU of vectors GINWF, XOGWF, PGFSigWF, or HAFPRigWF. Animals receiving two or more different vectors received a total of $2\times10^7$ TU and $3\times10^7$ TU vector, respectively.

Intraocular Pressure Measurements, Slit Lamp Examinations, & Gonioscopic Observation Prior to examinations, cats were anesthetized with 10 mg/kg intramuscular tiletamine HCl/zolazepam HCl (Telazol; Fort Dodge Laboratories Inc., Fort Dodge, Iowa) injection. Weekly examinations consisted of slit lamp (Haag-Streit, Mason, Ohio) observation and determination of intraocular pressure using a handheld pneumatonometer (Model 30 Classic; Medtronic, Fridley, Minn.).

Fluorescence of transduced TM was observed with a standard gonioscope (Posner; Ocular Instruments, Bellevue, Wash.) and a microscope (Eclipse E400; Nikon) equipped with a GFP-optimized filter (EF-4 B-2E/C FITC, cat. no. 96107; Nikon).

Results

Codon Optimization of Prostaglandin Pathway mRNAs

Initial studies revealed that human COX-2 and PGF receptor polypeptides were difficult to express using standard methods. By performing in silico analyses, it was discovered that the coding regions of both the COX-2 and PGF receptor mRNAs were aberrantly AU-rich, with a markedly suboptimal codon bias. The skewed codon use of the human COX-2 coding region is very similar in composition to that of lentiviral structural genes. This composition makes lentiviral mRNAs labile, a problem that the viruses overcome with specialized viral polypeptides that stabilize RNA at particular stages of the life cycle. The composition of the prostaglandin pathway mRNAs presumably fosters rapid endogenous turnover. Human codon-optimized versions of the human COX-2 cDNA (FIG. 1) and the PGF receptor cDNA were synthesized. The codon-optimized COX-2 cDNA contains a GC-rich sequence that encodes an amino acid sequence identical to the wild-type COX-2 sequence.

Figure 2:
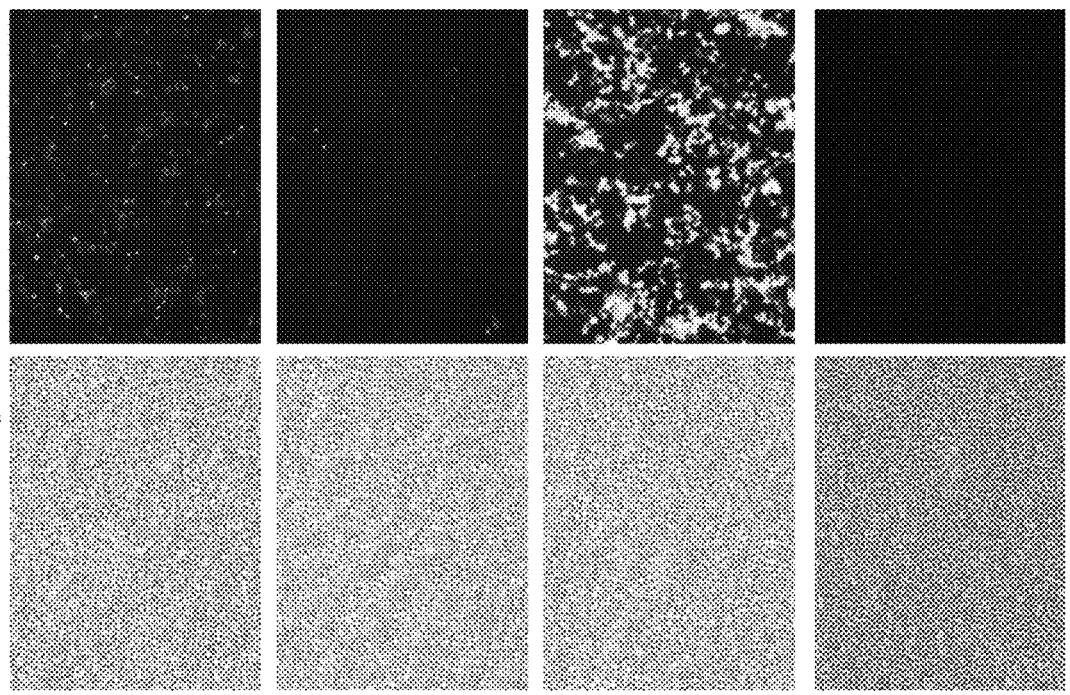
FIG. 2 contains photomicrographs of cells transfected with transfer constructs containing the wild-type COX-2 cDNA (COX2igWF) or the codon-optimized COX-2 cDNA (XOGWF) upstream of an IRES operably linked to a GFP coding sequence. Cells transfected with a transfer construct containing a GFP coding sequence operably linked to a CMV promoter (GINWF) served as a positive control, and mock transfected cells served as a negative control.

Transfer constructs were generated that contained the wild-type or the codon-optimized COX-2 cDNA upstream of an IRES operably linked to a GFP coding sequence. Cells were transfected with the constructs, and GFP expression levels were observed. A significantly higher level of GFP expression was observed in cells transfected with the construct containing the codon-optimized COX-2 cDNA (XOGWF) as compared to cells transfected with the construct containing the wild-type COX-2 cDNA (COX2igWF; FIG. 2).

Cells transfected with the transfer constructs containing the wild-type or codon-optimized COX-2 cDNA were also analyzed for mRNA levels by Northern blotting. The blots were analyzed with a GFP probe random-labeled using $^{32}$P-dCTP. The blots were also analyzed with a β-actin probe 5'-labeled using $^{32}$P-dATP to control for equal loading. The level of mRNA was much higher in cells transfected with the construct containing the codon-optimized COX-2 cDNA than in cells transfected with the construct containing the wild-type COX-2 cDNA (FIG. 3).

Figure 4:
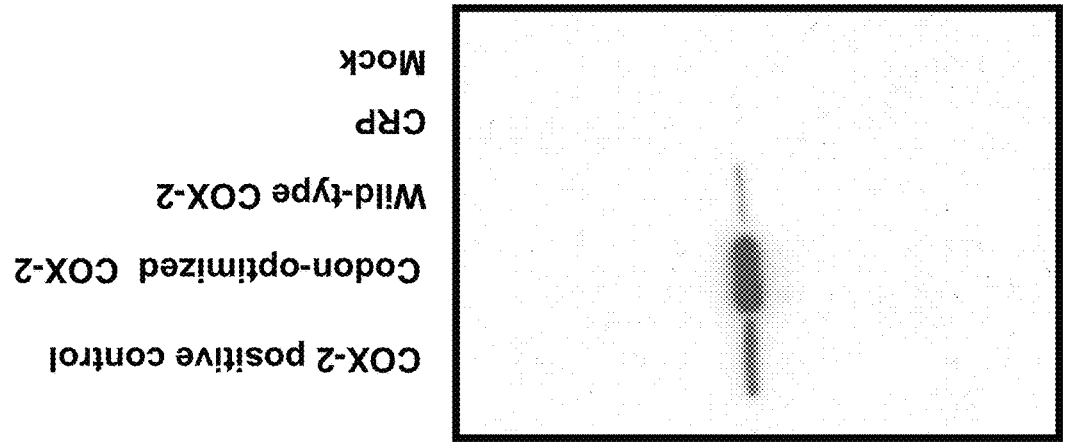
FIG. 4 is a Western blot analyzing expression of COX-2 polypeptides in 293T cells transfected with a transfer construct containing a codon-optimized or wild-type COX-2 cDNA.

Recombinant DNA constructs containing the codon-optimized COX-2 cDNA or the wild-type COX-2 cDNA were also used to transfect 293T cells, and lysates from the transfected cells were analyzed for COX-2 expression by Western blotting. Expression of COX-2 polypeptides was higher in cells transfected with the construct containing the codon-optimized COX-2 cDNA than in cells transfected with the construct containing the wild-type COX-2 cDNA (FIG. 4).

These results indicate that codon optimization of the COX-2 coding region increases the stability of the transcribed RNA, resulting in increased expression at the polypeptide level. The wild-type COX-2 coding region, not just the 3' untranslated region as was previously recognized, prevents significant polypeptide expression. In contrast, PGF synthase does not have an aberrant RNA base composition and does not require codon optimization.

Effect of the Expression of Prostaglandin Pathway Polypeptides on IOP In Vivo

Figure 5:
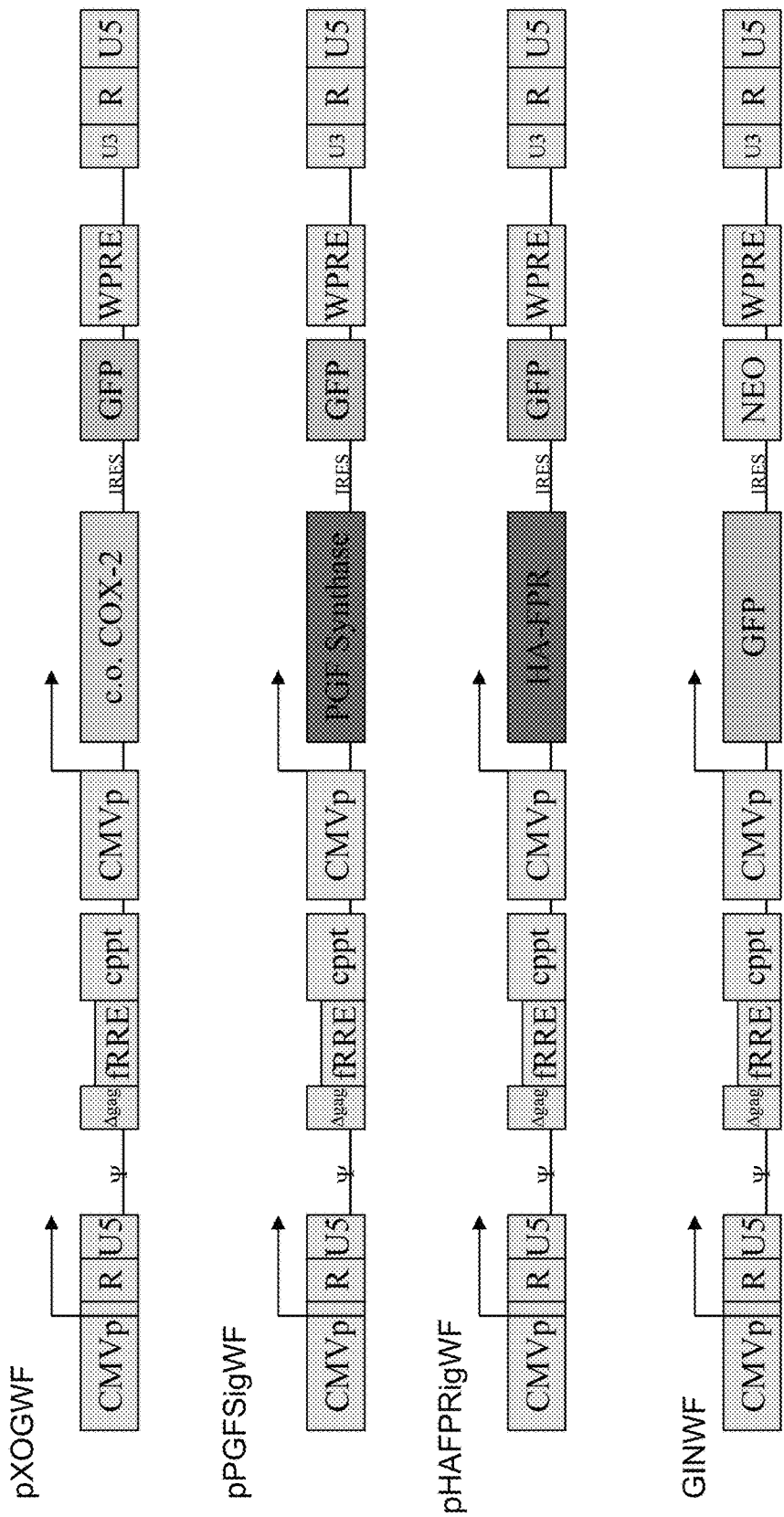
FIG. 5 is a schematic diagram of FIV-based lentiviral transfer constructs containing a codon-optimized COX-2 cDNA (pXOGWF), a PGF synthase cDNA (pPGFSigWF), or a codon-optimized prostaglandin F receptor cDNA (pHAFPRigWF). The prostaglandin F receptor cDNA was HA-tagged to enable detection of prostaglandin F receptor polypeptides on Western blots
Figure 6:
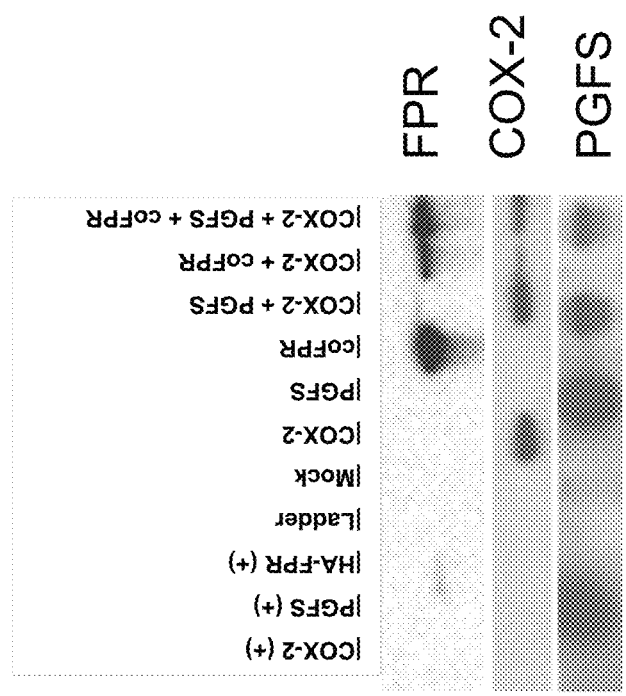
FIG. 6 is a Western blot analyzing expression of prostaglandin F receptor (FPR), COX-2, and prostaglandin F synthase (PGFS) polypeptides in cells that were mock transfected or transfected with one or more lentiviral transfer vectors containing a cDNA encoding an FPR, COX-2, or PGFS polypeptide.

Lentiviral transfer constructs based on the feline immunodeficiency virus (FIV) vector system (Poeschla et al., Nat. Med., 4(3):354-7 (1998)) were generated which contained a human codon-optimized COX-2 cDNA, a human PGF synthase cDNA, or a human codon-optimized PGF receptor cDNA (FIG. 5). Levels of COX-2, PGF synthase, and PGF receptor polypeptides in cells transfected with one or more of the transfer constructs were analyzed by Western blotting, and expression of each of the polypeptides was detected (FIG. 6).

Figure 7:
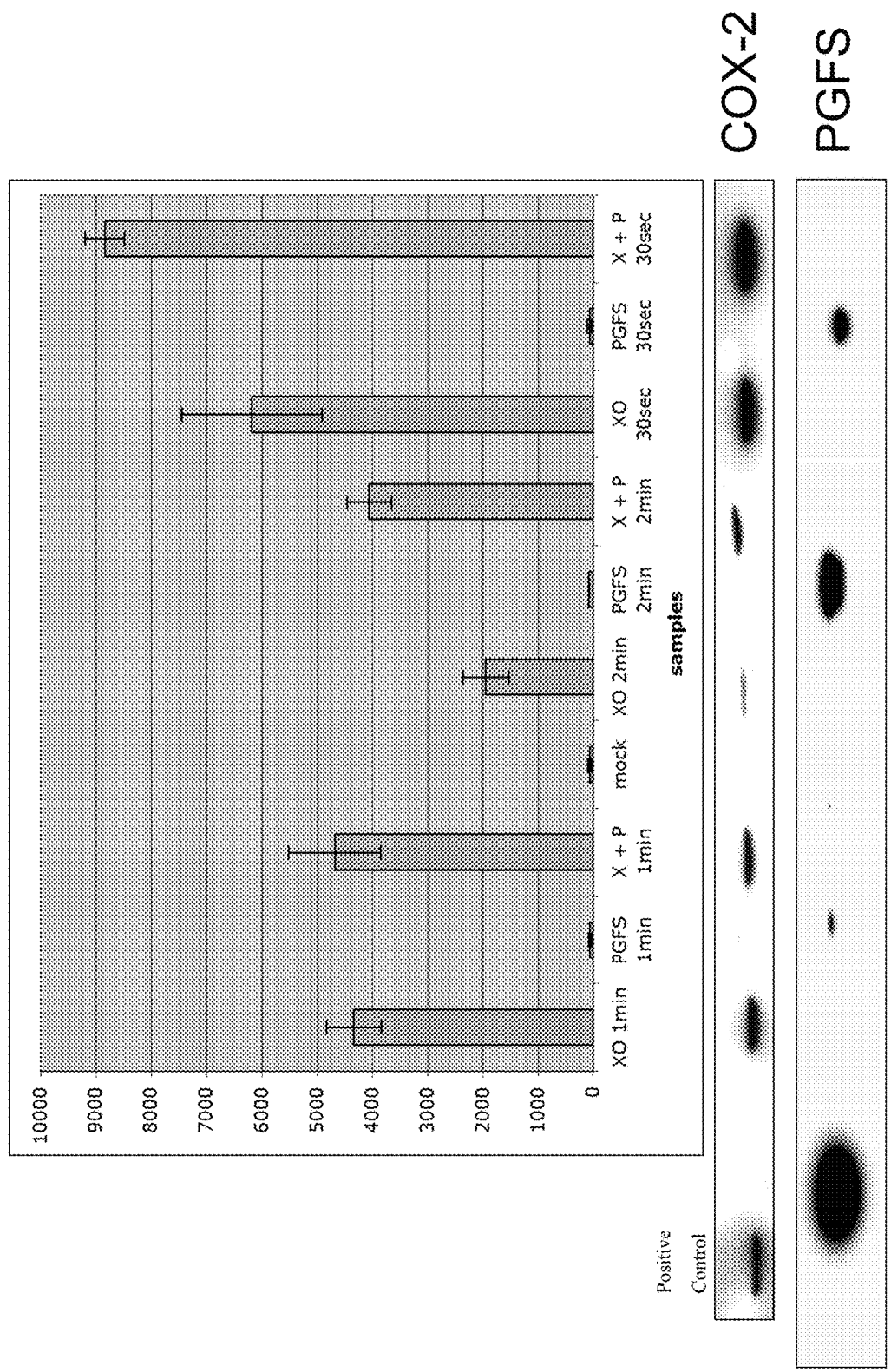
FIG. 7 is a graph plotting levels of PGF2alpha in 293T cells transfected with a construct containing a COX-2 cDNA, in 293T cells transfected with a construct containing a PGF synthase (PGFS) cDNA, and in 293T cells co-transfected with a construct containing a COX-2 cDNA and a construct containing a PGFS cDNA.

Production of PGF2alpha was measured in 293T cells transfected with a construct containing a COX-2 or a PGF synthase (PGFS) cDNA, and in 293T cells co-transfected with a construct containing a COX-2 cDNA and a construct containing a PGF synthase cDNA. Production of PGF2alpha was observed in the presence of COX-2 polypeptides and correlated strongly with the expression level of COX-2 polypeptides (FIG. 7). Co-expression of COX-2 and PGFS resulted in an even greater level of PGF2alpha production than expression of COX-2 alone (FIG. 7). Synthesis of PGF2alpha was increased up to $0.9 \times 10^4$-fold in the transfected cells relative to synthesis of PGF2alpha in control cells. Expression of PGFS alone did not increase PGF2alpha levels, indicating that COX-2 is a rate-limiting polypeptide in the prostaglandin synthesis pathway.

The effect of expression of prostaglandin pathway polypeptides on intraocular pressure (TOP) was investigated in a large animal model developed for glaucoma studies and described elsewhere (Loewen et al., Invest. Ophthalmol. Vis. Sci., 43(12):3686-90 (2002)). Fifteen domestic cats were divided into five groups, with three cats in each group. The anterior chamber of the right eye of each cat was injected with one or more lentiviral vectors containing a COX-2, PGFS, or prostaglandin F receptor (FPR) cDNA. The anterior chamber of the left eye of each cat was injected with $10^7$-$10^8$ TU of a control eGFP vector (FIG. 8). The animals were monitored serially for intraocular pressure (TOP) and clinical effects.

Figure 9:
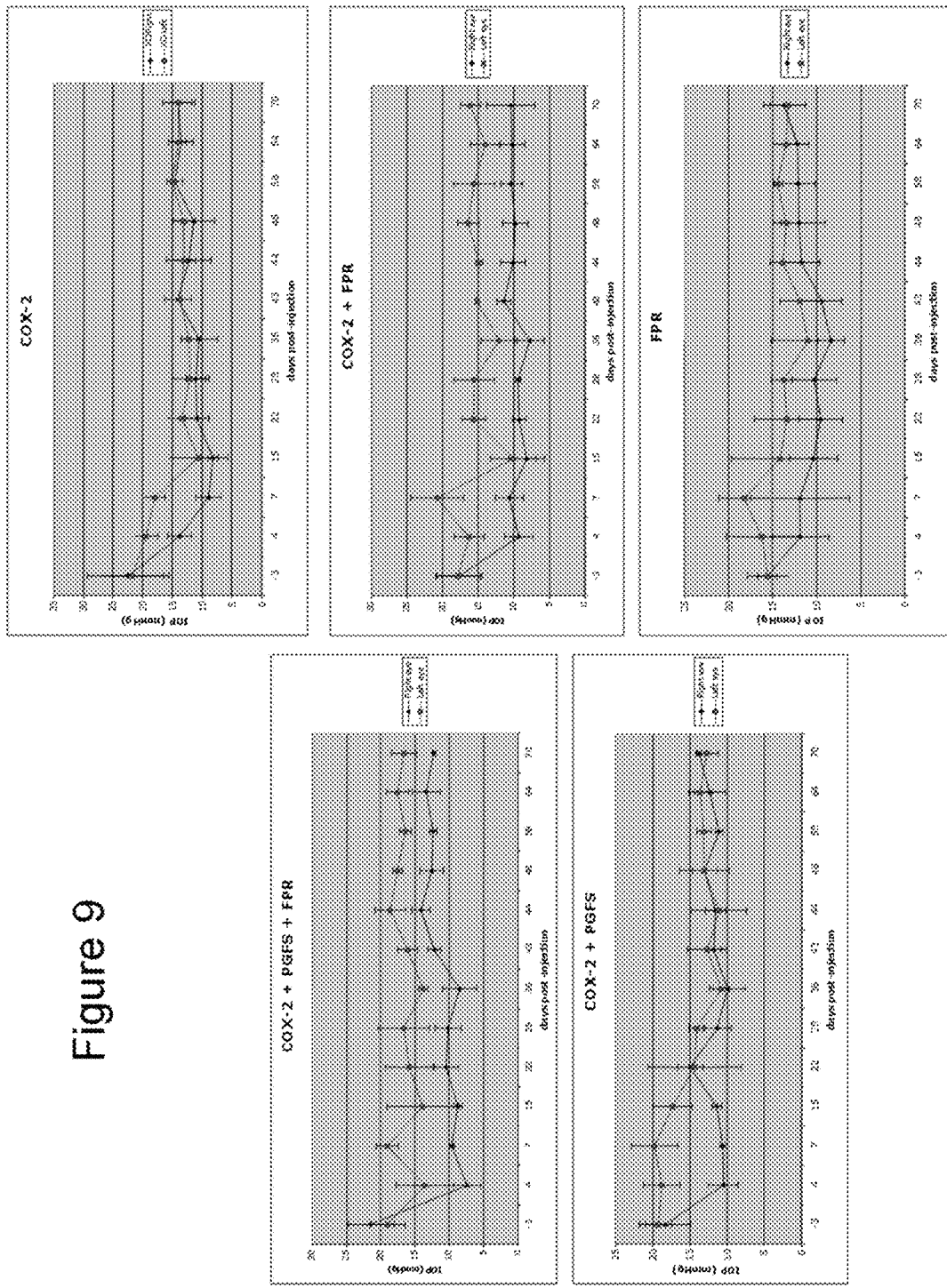
FIG. 9 contains a series of graphs plotting intraocular pressure (mm Hg) versus days post injection for the indicated treatment groups.
Figure 10:
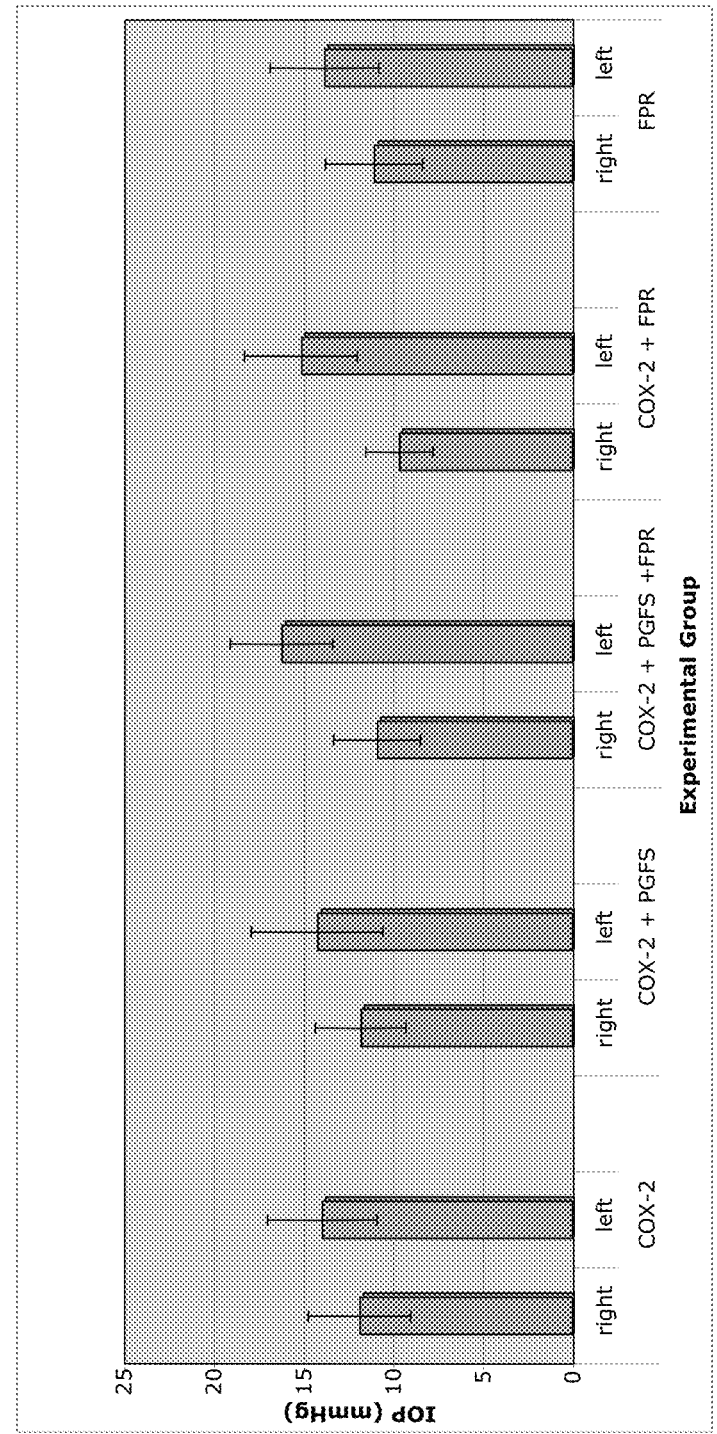
FIG. 10 is a graph plotting the mean intraocular pressure (TOP) sustained for more than two months in each of the five experimental groups described in FIG. 8 and in eyes treated with the control vector. The p-values were determined using a paired, two-tailed distribution T-test.

The lentiviral vectors were well-tolerated in the animals and produced marked, sustained (two months at present, with observation of all animals ongoing), and highly significant IOP decreases (the mean over the entire two months was 4.2 mm Hg, p<0.002) compared to the IOP levels in eyes treated with the control vector. A combination of vectors containing COX-2 and PGF receptor cDNAs produced the largest IOP decrease (mean=5.6 mm Hg, 38% reduction, $p<5\times10^{-14}$; FIGS. 9 and 10).

These results indicate that major prostaglandin biosynthetic and response pathways can be manipulated. Codon optimization of the COX-2 coding region profoundly augments mRNA stability. Sustained, substantial, highly statistically significant decreases in TOP were achieved in a large animal model.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing elevated intraocular pressure, said method comprising administering a viral vector to an eye of a mammal under conditions effective to reduce intraocular pressure of said eye, wherein said viral vector comprises a nucleic acid encoding a cyclooxygenase-2 polypeptide.

2. The method of claim 1, wherein said mammal is a human.

3. The method of claim 1, wherein said administering comprises contacting said eye with a solution containing said viral vector.

4. The method of claim 1, wherein said method is effective to reduce said intraocular pressure by at least 10 percent.

5. The method of claim 1, wherein said method is effective to reduce said intraocular pressure by at least 20 percent.

6. The method of claim 1, wherein said method is effective to reduce said intraocular pressure by at least 30 percent.

7. The method of claim 1, wherein said viral vector is a lentiviral vector.

8. The method of claim 1, wherein said polypeptide is a human cyclooxygenase-2 polypeptide, and wherein said nucleic acid encoding said polypeptide is codon-optimized for use in mammalian cells.

* * * * *

SEQUENCE LISTING

```
<160> NUMBER OF SEQ ID NOS: 12

<210> SEQ ID NO 1
<211> LENGTH: 604
<212> TYPE: PRT
<213> ORGANISM: Homo sapiens

<400> SEQUENCE: 1

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
```

```
                    35                  40                  45
Phe Tyr Gly Glu Asn Cys Ser Thr Pro Glu Phe Leu Thr Arg Ile Lys
 50                  55                  60

Leu Phe Leu Lys Pro Thr Pro Asn Thr Val His Tyr Ile Leu Thr His
 65                  70                  75                  80

Phe Lys Gly Phe Trp Asn Val Val Asn Asn Ile Pro Phe Leu Arg Asn
                 85                  90                  95

Ala Ile Met Ser Tyr Val Leu Thr Ser Arg Ser His Leu Ile Asp Ser
                100                 105                 110

Pro Pro Thr Tyr Asn Ala Asp Tyr Gly Tyr Lys Ser Trp Glu Ala Phe
                115                 120                 125

Ser Asn Leu Ser Tyr Tyr Thr Arg Ala Leu Pro Pro Val Pro Asp Asp
                130                 135             140

Cys Pro Thr Pro Leu Gly Val Lys Gly Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Ala Gln His Phe Thr
                180                 185                 190

His Gln Phe Phe Lys Thr Asp His Lys Arg Gly Pro Ala Phe Thr Asn
                195                 200                 205

Gly Leu Gly His Gly Val Asp Leu Asn His Ile Tyr Gly Glu Thr Leu
                210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
                275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Lys Gln Phe Gln Tyr Gln Asn Arg Ile Ala Ala Glu Phe Asn
                355                 360                 365

Thr Leu Tyr His Trp His Pro Leu Leu Pro Asp Thr Phe Gln Ile His
                370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
                435                 440                 445

Phe Asn Glu Tyr Arg Lys Arg Phe Met Leu Lys Pro Tyr Glu Ser Phe
450                 455                 460
```

```
Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Arg Ser Gly Leu Asp Asp Ile Asn
                580                 585                 590

Pro Thr Val Leu Leu Lys Glu Arg Ser Thr Glu Leu
        595                 600
```

```
<210> SEQ ID NO 2
<211> LENGTH: 1815
<212> TYPE: DNA
<213> ORGANISM: Homo sapiens

<400> SEQUENCE: 2
atgctcgccc gcgccctgct gctgtgcgcg gtcctggcgc tcagccatac agcaaatcct      60
tgctgttccc acccatgtca aaaccgaggt gtatgtatga gtgtgggatt tgaccagtat     120
aagtgcgatt gtacccggac aggattctat ggagaaaact gctcaacacc ggaatttttg     180
acaagaataa aattatttct gaaacccact ccaaacacag tgcactacat acttacccac     240
ttcaagggat tttggaacgt tgtgaataac attcccttcc ttcgaaatgc aattatgagt     300
tatgtcttga catccagatc acatttgatt gacagtccac caacttacaa tgctgactat     360
ggctacaaaa gctgggaagc cttctctaac ctctcctatt atactagagc ccttcctcct     420
gtgcctgatg attgcccgac tcccttgggt gtcaaaggta aaagcagct tcctgattca     480 aatgagattg tggaaaaatt gcttctaaga gaaagttca tccctgatcc ccagggctca     540
aacatgatgt ttgcattctt tgcccagcac ttcacgcatc agttttttcaa gacagatcat     600 aagcgagggc cagcttttcac caacgggctg gccatgggg tggacttaaa tcatatttac     660
ggtgaaactc tggctagaca gcgtaaactg cgccttttca aggatggaaa aatgaaatat     720
cagataattg atggagagat gtatcctccc acagtcaaag atactcaggc agagatgatc     780
taccctcctc aagtccctga gcatctacgg tttgctgtgg ggcaggaggt ctttggtctg     840
gtgcctggtc tgatgatgta tgccacaatc tggctgcggg aacacaacag agtatgcgat     900
gtgcttaaac aggagcatcc tgaatggggt gatgagcagt tgttccagac aagcaggcta     960
atactgatag agagactat taagattgtg attgaagatt atgtgcaaca cttgagtggc    1020
tatcacttca aactgaaatt tgacccagaa ctactttttca caaacaatt ccagtaccaa    1080 aatcgtattg ctgctgaatt aacaccctc tatcactggc atccccttct gcctgacacc    1140
tttcaaattc atgaccagaa atacaactat caacagttta tctacaacaa ctctatattg    1200
ctggaacatg gaattaccca gtttgttgaa tcattcacca ggcaaattgc tggcagggtt    1260
gctggtggta ggaatgttcc acccgcagta cagaaagtat cacaggcttc cattgaccag    1320
```

| | |
|---|---|
| agcaggcaga tgaaatacca gtcttttaat gagtaccgca aacgctttat gctgaagccc | 1380 |
| tatgaatcat ttgaagaact tacaggagaa aaggaaatgt ctgcagagtt ggaagcactc | 1440 |
| tatggtgaca tcgatgctgt ggagctgtat cctgcccttc tggtagaaaa gcctcggcca | 1500 |
| gatgccatct ttggtgaaac catggtagaa gttggagcac cattctcctt gaaaggactt | 1560 |
| atgggtaatg ttatatgttc tcctgcctac tggaagccaa gcacttttgg tggagaagtg | 1620 |
| ggttttcaaa tcatcaacac tgcctcaatt cagtctctca tctgcaataa cgtgaagggc | 1680 |
| tgtcccttta cttcattcag tgttccagat ccagagctca ttaaaacagt caccatcaat | 1740 |
| gcaagttctt cccgctccgg actagatgat atcaatccca cagtactact aaaagaacgt | 1800 |
| tcgactgaac tgtag | 1815 |

<210> SEQ ID NO 3
<211> LENGTH: 1815
<212> TYPE: DNA
<213> ORGANISM: Artificial Sequence
<220> FEATURE:
<223> OTHER INFORMATION: codon optimized COX-2 nucleic acid sequence

<400> SEQUENCE: 3

| | |
|---|---|
| atgctcgctc gggctctgct cctgtgcgct gtgctggctc tcagccacac cgctaacccc | 60 |
| tgctgcagcc acccctgcca gaaccggggc gtgtgcatga cgtgggcttc gaccagtac | 120 |
| aagtgcgatt gcacccggac cggcttctac ggcgaaaact gcagcacccc cgagttcctg | 180 |
| acccggatca aactgttcct gaaacccacc cccaacaccg tgcactacat cctgacccac | 240 |
| ttcaagggct ctggaacgt ggtgaacaac atccccttcc tgcggaacgc tatcatgagc | 300 |
| tacgtgctga ccagccggag ccacctgatc gatagccctc caacctacaa cgctgactac | 360 |
| ggctacaaaa gctgggaagc cttcagcaac ctcagctact acacccgggc tctgcctccc | 420 |
| gtgcccgatg attgccccac ccctctgggc gtgaaaggca gaagcagct gcccgatagc | 480 |
| aacgagatcg tggaaaaact gctcctgcgg cggaagttca tccccgatcc ccagggcagc | 540 |
| aacatgatgt tcgcttttct tcgcccagcac ttcacccacc agttcttcaa gaccgatcac | 600 |
| aaacggggcc ccgccttcac caacggcctg ggccacggcg tggacctgaa ccacatctac | 660 |
| ggcgaaaccc tggctcggca gcggaaactg cggctgttca aggatggcaa aatgaaatac | 720 |
| cagatcatcg atggcgagat gtaccctccc accgtgaaag ataccaggc tgaaatgatc | 780 |
| tacccccccc aggtgcccga cacctgcgg ttcgctgtgg ccaggaagt gttcggcctg | 840 |
| gtgccggc tgatgatgta cgctaccatc tggctgcggg aacacaaccg ggtgtgcgat | 900 |
| gtgctgaaac aggaacaccc cgaatggggc gatgaacagc tgttccagac cagccggctg | 960 |
| atcctgatcg gcgagaccat caagatcgtg atcgaagatt acgtgcagca cctgagcggc | 1020 |
| taccacttca acactgaaatt cgaccccgaa ctgctcttca caaacagtt ccagtaccag | 1080 |
| aaccggatcc ctgccgagtt caacaccctc taccactggc accccctgct ccccgacacc | 1140 |
| ttccagatcc acgaccagaa atacaactac cagcagttca tctacaacaa cagcatcctg | 1200 |
| ctcgaacacg gcatcaccca gttcgtggaa agcttcaccc ggcagatcgc tggccgggtg | 1260 |
| gctggcggcc ggaacgtgcc tcctgccgtg cagaaagtga gccaggctag catcgaccag | 1320 |
| agccggcaga tgaaatacca gagcttcaac gagtaccgga acggttcat gctgaagccc | 1380 |
| tacgaaagct cgaagagct gaccggcgaa aaggaaatga cgctgaact ggaagctctg | 1440 |
| tacggcgaca tcgatgctgt ggaactgtac cccgcccctc tggtggagaa accccggccc | 1500 |

-continued

```
gatgccatct tcggcgaaac catggtggaa gtgggcgctc ccttcagcct gaaaggcctg    1560
atgggcaacg tgatctgcag ccccgcttac tggaaaccca gcaccttcgg cggcgaagtg    1620
ggcttccaga tcatcaacac cgccagcatc cagagcctca tctgcaacaa cgtgaaaggc    1680
tgccccttca ccagcttcag cgtgcccgat cccgagctca tcaaaaccgt gaccatcaac    1740
gctagcagca gccggagcgg cctggatgac atcaaccccà ccgtgctgct caaagaacgg    1800
agcaccgaac tgtga                                                     1815
```

<210> SEQ ID NO 4
<211> LENGTH: 368
<212> TYPE: PRT
<213> ORGANISM: Homo sapiens
<220> FEATURE:
<223> OTHER INFORMATION: codon optimized COX-2 nucleic acid sequence
<400> SEQUENCE: 4

```
Met Tyr Pro Tyr Asp Val Pro Asp Tyr Ala Ser Met Asn Asn Ser Lys
1               5                   10                  15

Gln Leu Val Ser Pro Ala Ala Ala Leu Leu Ser Asn Thr Thr Cys Gln
            20                  25                  30

Thr Glu Asn Arg Leu Ser Val Phe Phe Ser Val Ile Phe Met Thr Val
        35                  40                  45

Gly Ile Leu Ser Asn Ser Leu Ala Ile Ala Ile Leu Met Lys Ala Tyr
    50                  55                  60

Gln Arg Phe Arg Gln Lys Ser Lys Ala Ser Phe Leu Leu Leu Ala Ser
65                  70                  75                  80

Gly Leu Val Ile Thr Asp Phe Phe Gly His Leu Ile Asn Gly Ala Ile
                85                  90                  95

Ala Val Phe Val Tyr Ala Ser Asp Lys Glu Trp Ile Arg Phe Asp Gln
            100                 105                 110

Ser Asn Val Leu Cys Ser Ile Phe Gly Ile Cys Met Val Phe Ser Gly
        115                 120                 125

Leu Cys Pro Leu Leu Leu Gly Ser Val Met Ala Ile Glu Arg Cys Ile
    130                 135                 140

Gly Val Thr Lys Pro Ile Phe His Ser Thr Lys Ile Thr Ser Lys His
145                 150                 155                 160

Val Lys Met Met Leu Ser Gly Val Cys Leu Phe Ala Val Phe Ile Ala
                165                 170                 175

Leu Leu Pro Ile Leu Gly His Arg Asp Tyr Lys Ile Gln Ala Ser Arg
            180                 185                 190

Thr Trp Cys Phe Tyr Asn Thr Glu Asp Ile Lys Asp Trp Glu Asp Arg
        195                 200                 205

Phe Tyr Leu Leu Leu Phe Ser Phe Leu Gly Leu Leu Ala Leu Gly Val
    210                 215                 220

Ser Leu Leu Cys Asn Ala Ile Thr Gly Ile Thr Leu Leu Arg Val Lys
225                 230                 235                 240

Phe Lys Ser Gln Gln His Arg Gln Gly Arg Ser His His Leu Glu Met
                245                 250                 255

Val Ile Gln Leu Leu Ala Ile Met Cys Val Ser Cys Ile Cys Trp Ser
            260                 265                 270

Pro Phe Leu Val Thr Met Ala Asn Ile Gly Ile Asn Gly Asn His Ser
        275                 280                 285

Leu Glu Thr Cys Glu Thr Thr Leu Phe Ala Leu Arg Met Ala Thr Trp
    290                 295                 300
```

```
Asn Gln Ile Leu Asp Pro Trp Val Tyr Ile Leu Leu Arg Lys Ala Val
305                 310                 315                 320

Leu Lys Asn Leu Tyr Lys Leu Ala Ser Gln Cys Cys Gly Val His Val
            325                 330                 335

Ile Ser Leu His Ile Trp Glu Leu Ser Ser Ile Lys Asn Ser Leu Lys
            340                 345                 350

Val Ala Ala Ile Ser Glu Ser Pro Val Ala Glu Lys Ser Ala Ser Thr
            355                 360                 365
```

<210> SEQ ID NO 5
<211> LENGTH: 1107
<212> TYPE: DNA
<213> ORGANISM: Homo sapiens

<400> SEQUENCE: 5

```
atgtatccat atgatgtgcc agattatgct tccatgaaca attccaaaca gctagtgtct      60
cctgcagctg cgcttctttc aaacacaacc tgccagacgg aaaaccggct ttccgtattt     120
ttttcagtaa tcttcatgac agtgggaatc ttgtcaaaca gccttgccat cgccattctc     180
atgaaggcat atcagagatt tagacagaag tccaaggcat cgtttctgct tttggccagc     240
ggcctggtaa tcactgattt cttttggcca tctcatcaatg gagccatagc agtatttgta     300
tatgcttctg ataaagaatg gatccgcttt gaccaatcaa atgtcctttg cagtattttt     360
ggtatctgca tggtgttttc tggtctgtgc ccacttcttc taggcagtgt gatggccatt     420
gagcggtgta ttggagtcac aaaaccaata tttcattcta cgaaaattac atccaaacat     480
gtgaaaatga tgttaagtgg tgtgtgcttg tttgctgttt tcatagcttt gctgcccatc     540
cttggacatc gagactataa aattcaggcg tcgaggacct ggtgtttcta acacacagaa     600
gacatcaaag actgggaaga tagatttat cttctacttt tttctttcct ggggctctta     660
gcccttggtg tttcattgtt gtgcaatgca atcacaggaa ttacactttt aagagttaaa     720
tttaaaagtc agcagcacag acaaggcaga tctcatcatt tggaaatggt aatccagctc     780
ctggcgataa tgtgtgtctc ctgtatttgt tggagcccat ttctggttac aatggccaac     840
attggaataa atggaaatca ttctctggaa acctgtgaaa caacacttt tgctctccga     900
atggcaacat ggaatcaaat cttagatcct tgggtatata ttcttctacg aaaggctgtc     960
cttaagaatc tctataagct tgccagtcaa tgctgtggag tgcatgtcat cagcttacat    1020
atttgggagc ttagttccat taaaaattcc ttaaaggttg ctgctatttc tgagtcacca    1080
gttgcagaga aatcagcaag cacctag                                        1107
```

<210> SEQ ID NO 6
<211> LENGTH: 1107
<212> TYPE: DNA
<213> ORGANISM: Artificial Sequence
<220> FEATURE:
<223> OTHER INFORMATION: codon optimized human prostaglandin F2a
      receptor polypeptide

<400> SEQUENCE: 6

```
atgtaccct atgacgtgcc agattacgcc tccatgaaca attccaaaca gctcgtgtca       60
cccgcagctg cactgctctc taatacaaca tgccagaccg agaataggct cagcgtgttt     120
ttctctgtga tctttatgac tgtgggcatc ctcagcaact cactggctat cgcaattctg     180
atgaaggcct accagcgctt cgacagaaag agtaaggcct cttttcctcc tctggccagc     240
gggctggtca ttaccgactt tttcggacac ctcatcaatg gagccattgc tgtgttcgtc     300
```

-continued

| | |
|---|---|
| tatgcctccg ataaggagtg gattagattc gatcagtcaa acgtgctctg ttcaatcttt | 360 |
| ggtatctgta tggtcttttc aggtctctgc cctctgctgc tgggctccgt gatggccatt | 420 |
| gagcgctgta ttggcgtgac caagcctatc tttcattcta caaagatcac ctccaagcac | 480 |
| gtgaagatga tgctgagcgg ggtgtgcctc ttcgctgtct tcattgcact gctgccaatt | 540 |
| ctcggccacc gggattacaa gatccaggca tcccgaacct ggtgcttcta caataccgaa | 600 |
| gacatcaaag attgggagga taggttctac ctgctcctct ttagtttcct gggcctgctg | 660 |
| gctctcggag tgtccctgct gtgtaacgcc atcacaggca tcaccctgct gagagtgaag | 720 |
| tttaagtctc agcagcatag acagggcaga agccaccacc tcgagatggt catccagctg | 780 |
| ctggccatca tgtgcgtgtc ttgcatctgt tggtctccct tcctggtcac aatggccaac | 840 |
| attgggatta tggtaatca cagcctggaa acatgcgaaa caacactgtt tgccctgaga | 900 |
| atggcaacct ggaatcagat tctggaccca tgggtgtaca tcctgctcag aaaagccgtg | 960 |
| ctgaaaaatc tctacaagct agccagccag tgctgcggcg tgcacgtgat cagcctgcac | 1020 |
| atctgggagc tgagcagcat caagaacagc ctgaaggtgg ccgccatcag cgagagcccc | 1080 |
| gtggccgaga agagcgccag cacctga | 1107 |

<210> SEQ ID NO 7
<211> LENGTH: 323
<212> TYPE: PRT
<213> ORGANISM: Homo sapiens

<400> SEQUENCE: 7

Met Asp Ser Lys Gln Gln Cys Val Lys Leu Asn Asp Gly His Phe Met
1               5                   10                  15

Pro Val Leu Gly Phe Gly Thr Tyr Ala Pro Glu Val Pro Arg Ser
            20                  25                  30

Lys Ala Leu Glu Val Thr Lys Leu Ala Ile Glu Ala Gly Phe Arg His
        35                  40                  45

Ile Asp Ser Ala His Leu Tyr Asn Asn Glu Glu Gln Val Gly Leu Ala
    50                  55                  60

Ile Arg Ser Lys Ile Ala Asp Gly Ser Val Lys Arg Glu Asp Ile Phe
65                  70                  75                  80

Tyr Thr Ser Lys Leu Trp Ser Thr Phe His Arg Pro Glu Leu Val Arg
                85                  90                  95

Pro Ala Leu Glu Asn Ser Leu Lys Lys Ala Gln Leu Asp Tyr Val Asp
            100                 105                 110

Leu Tyr Leu Ile His Ser Pro Met Ser Leu Lys Pro Gly Glu Glu Leu
        115                 120                 125

Ser Pro Thr Asp Glu Asn Gly Lys Val Ile Phe Asp Ile Val Asp Leu
    130                 135                 140

Cys Thr Thr Trp Glu Ala Met Glu Lys Cys Lys Asp Ala Gly Leu Ala
145                 150                 155                 160

Lys Ser Ile Gly Val Ser Asn Phe Asn Arg Arg Gln Leu Glu Met Ile
                165                 170                 175

Leu Asn Lys Pro Gly Leu Lys Tyr Lys Pro Val Cys Asn Gln Val Glu
            180                 185                 190

Cys His Pro Tyr Phe Asn Arg Ser Lys Leu Leu Asp Phe Cys Lys Ser
        195                 200                 205

Lys Asp Ile Val Leu Val Ala Tyr Ser Ala Leu Gly Ser Gln Arg Asp
    210                 215                 220

Lys Arg Trp Val Asp Pro Asn Ser Pro Val Leu Leu Glu Asp Pro Val

```
                225                 230                 235                 240
Leu Cys Ala Leu Ala Lys Lys His Lys Arg Thr Pro Ala Leu Ile Ala
                    245                 250                 255

Leu Arg Tyr Gln Leu Gln Arg Gly Val Val Leu Ala Lys Ser Tyr
                260                 265                 270

Asn Glu Gln Arg Ile Arg Gln Asn Val Gln Val Phe Glu Phe Gln Leu
            275                 280                 285

Thr Ala Glu Asp Met Lys Ala Ile Asp Gly Leu Asp Arg Asn Leu His
        290                 295                 300

Tyr Phe Asn Ser Asp Ser Phe Ala Ser His Pro Asn Tyr Pro Tyr Ser
305                 310                 315                 320

Asp Glu Tyr

<210> SEQ ID NO 8
<211> LENGTH: 972
<212> TYPE: DNA
<213> ORGANISM: Homo sapiens

<400> SEQUENCE: 8
atggattcca acagcagtg tgtaaagcta aatgatggcc acttcatgcc tgtattggga      60
tttggcacct atgcacctcc agaggttccg agaagtaaag ctttggaggt cacaaaatta     120
gcaatagaag ctgggttccg ccatatagat tctgctcatt atacaataa tgaggagcag      180 gttggactgg ccatccgaag caagattgca gatggcagtg tgaagagaga agacatattc     240
tacacttcaa agctttggtc cacttttcat cgaccagagt tggtccgacc agccttggaa     300
aactcactga aaaagctca attggactat gttgacctct atcttattca ttctccaatg     360
tctctaaagc caggtgagga actttcacca acagatgaaa atggaaaagt aatatttgac     420
atagtggatc tctgtaccac ctgggaggcc atggagaagt gtaaggatgc aggattggcc     480
aagtccattg gggtgtcaaa cttcaaccgc aggcagctgg agatgatcct caacaagcca     540
ggactcaagt acaagcctgt ctgcaaccag gtagaatgtc atccgtattt caaccggagt     600
aaattgctag atttctgcaa gtcgaaagat attgttctgg ttgcctatag tgctctggga     660
tctcaacgag acaaacgatg ggtggacccg aactccccgg tgctcttgga ggacccagtc     720
ctttgtgcct tggcaaaaaa gcacaagcga accccagccc tgattgccct gcgctaccag     780
ctgcagcgtg gggttgtggt cctggccaag agctacaatg agcagcgcat cagacagaac     840
gtgcaggttt ttgagttcca gttgactgca gaggacatga agccataga tggcctagac     900 agaaatctcc actatttaa cagtgatagt tttgctagcc accctaatta tccatattca     960
gatgaatatt aa                                                         972

<210> SEQ ID NO 9
<211> LENGTH: 386
<212> TYPE: PRT
<213> ORGANISM: Homo sapiens

<400> SEQUENCE: 9

Met Ala Asp Ser Cys Arg Asn Leu Thr Tyr Val Arg Gly Ser Val Gly
1               5                   10                  15

Pro Ala Thr Ser Thr Leu Met Phe Val Ala Gly Val Val Gly Asn Gly
                20                  25                  30

Leu Ala Leu Gly Ile Leu Ser Ala Arg Arg Pro Ala Arg Pro Ser Ala
            35                  40                  45

Phe Ala Val Leu Val Thr Gly Leu Ala Ala Thr Asp Leu Leu Gly Thr
```

| | | | | | | | | | | | | |
|---|---|---|---|---|---|---|---|---|---|---|---|---|
| | | 50 | | | 55 | | | 60 | | | | |
| Ser | Phe | Leu | Ser | Pro | Ala | Val | Phe | Val | Ala | Tyr | Ala | Arg | Asn | Ser | Ser |
| 65 | | | | 70 | | | | 75 | | | | 80 |

Ser Phe Leu Ser Pro Ala Val Phe Val Ala Tyr Ala Arg Asn Ser Ser
65                  70                  75                  80

Leu Leu Gly Leu Ala Arg Gly Gly Pro Ala Leu Cys Asp Ala Phe Ala
                85                  90                  95

Phe Ala Met Thr Phe Phe Gly Leu Ala Ser Met Leu Ile Leu Phe Ala
            100                 105                 110

Met Ala Val Glu Arg Cys Leu Ala Leu Ser His Pro Tyr Leu Tyr Ala
        115                 120                 125

Gln Leu Asp Gly Pro Arg Cys Ala Arg Leu Ala Leu Pro Ala Ile Tyr
    130                 135                 140

Ala Phe Cys Val Leu Phe Cys Ala Leu Pro Leu Leu Gly Leu Gly Gln
145                 150                 155                 160

His Gln Gln Tyr Cys Pro Gly Ser Trp Cys Phe Leu Arg Met Arg Trp
                165                 170                 175

Ala Gln Pro Gly Gly Ala Ala Phe Ser Leu Ala Tyr Ala Gly Leu Val
            180                 185                 190

Ala Leu Leu Val Ala Ala Ile Phe Leu Cys Asn Gly Ser Val Thr Leu
        195                 200                 205

Ser Leu Cys Arg Met Tyr Arg Gln Gln Lys Arg His Gln Gly Ser Leu
    210                 215                 220

Gly Pro Arg Pro Arg Thr Gly Glu Asp Glu Val Asp His Leu Ile Leu
225                 230                 235                 240

Leu Ala Leu Met Thr Val Val Met Ala Val Cys Ser Leu Pro Leu Thr
                245                 250                 255

Ile Arg Cys Phe Thr Gln Ala Val Ala Pro Asp Ser Ser Ser Glu Met
            260                 265                 270

Gly Asp Leu Leu Ala Phe Arg Phe Tyr Ala Phe Asn Pro Ile Leu Asp
        275                 280                 285

Pro Trp Val Phe Ile Leu Phe Arg Lys Ala Val Phe Gln Arg Leu Lys
    290                 295                 300

Leu Trp Val Cys Cys Leu Cys Leu Gly Pro Ala His Gly Asp Ser Gln
305                 310                 315                 320

Thr Pro Leu Ser Gln Leu Ala Ser Gly Arg Arg Asp Pro Arg Ala Pro
                325                 330                 335

Ser Ala Pro Val Gly Lys Glu Gly Ser Cys Val Pro Leu Ser Ala Trp
            340                 345                 350

Gly Glu Gly Gln Val Glu Pro Leu Pro Pro Thr Gln Gln Ser Ser Gly
        355                 360                 365

Ser Ala Val Gly Thr Ser Ser Lys Ala Glu Ala Ser Val Ala Cys Ser
    370                 375                 380

Leu Cys
385

<210> SEQ ID NO 10
<211> LENGTH: 2103
<212> TYPE: DNA
<213> ORGANISM: Homo sapiens

<400> SEQUENCE: 10
aagctgacac acagaccgac acaggcagcg agagacacga ggagcaaagc aagtgaaggc    60
acagacgcac gggacaggag agcctgggca agactggaga gcccagacct gggatggcgg    120
attcgtgcag gaacctcacc tacgtgcggg gctcggtggg gccggccacc agcaccctga    180

```
tgttcgtggc cggtgtggtg ggcaacgggc tggccctggg catcctgagc gcacggcgac      240
cggcgcgccc ctcggccttc gcggtgctgg tgaccggact ggcggccacc gacctgctgg      300
gcaccagctt cctgagcccg gccgtgttcg tggcctatgc gcgcaacagc tccctgctgg      360
gcctggcccg aggcggcccc gccctgtgcg atgccttcgc cttcgccatg accttcttcg      420
gcctggcgtc catgctcatc ctctttgcca tggccgtgga gcgctgcctg cgctgagcc       480 accctaccct ctacgcgcag ctggacgggc ccgctgcgc cgcctggcg ctgccagcca        540 tctacgcctt ctgcgtcctc ttctgcgcgc tgcccctgct gggcctgggc aacaccagc       600 agtactgccc cggcagctgg tgcttcctcc gcatgcgctg ggcccagccg gcggcgccg       660 ccttctcgct ggcctacgcc ggcctggtgg ccctgctggt ggctgccatc ttcctctgca      720
acggctcggt caccctcagc ctctgccgca tgtaccgcca gcagaagcgc accagggct       780 ctctgggtcc acggccgcgc accggagagg acgaggtgga ccacctgatc ctgctggccc      840
tcatgacagt ggtcatggcc gtgtgctccc tgcctctcac gatccgctgc ttcacccagg      900
ctgtcgcccc tgacagcagc agtgagatgg gggacctcct tgccttccgc ttctacgcct      960
tcaaccccat cctggacccc tgggtcttca tccttttccg caaggctgtc ttccagcgac      1020
tcaagctctg ggtctgctgc ctgtgcctcg gcctgccca cggagactcg cagacacccc      1080
tttcccagct cgcctcaggg aggagggacc caagggcccc ctctgctcct gtgggaaagg      1140
aggggagctg cgtgcctttg tcggcttggg gcgaggggca ggtggagccc ttgcctccca      1200
cacagcagtc cagcggcagc gccgtgggaa cgtcgtccaa agcagaagcc agcgtcgcct      1260
gctccctctg ctgacatttc aagctgaccc tgtgatctct gccctgtctt cgggcgacag      1320
gagccagaaa atcagggaca tggctgatgg ctgcggatgc tggaaccttg ccccccaaac      1380
tctggggccg atcagctgct gtttctcctg cggcagggca gtcgctgctg gctctgggaa      1440
gagagtgagg gacagaggaa acgtttatcc tggagtgcag aaagaatggt tctctcaaaa      1500
taaccagtgg cctggccgac ctgctctggc cctggattcc ccatccatct cattgtctaa      1560
atatttagaa ggcggagaag ttcccagagg cttctgtaca gtcaggtctg ctctggtctg      1620
ggtgctggct ccaatctgcg tccacttagg aggcccaact gcccaccca agtcccagg       1680 ggatggccct cccctctac caagccactc caagagccag cccctttctg ctccacaaaa       1740
accacagtta ttggaaaagc tccctgcctt cccttgccgc tggtccccca ccaggcttgg     1800
gagccctggc atcccaaagg ggcaacggga ggaaggggag gctgctgcat gtgggtgat       1860 gacgtaggac atgtgcttgg tacaaaaagg gcctagacac ttccacctag cttgactggc      1920
tgcaagatga gaactggggg ggtgcaggtg gtggggagac agatggagaa gctggcagat      1980
gaagggtggg ggctgcggat cccagggact gccccagaac acaaacctaa gtcctgtgcc      2040
tgtccccagg gtcctgaata aataaaagcc tccttgcaga gcctgaaaaa aaaaaaaaa      2100 aaa                                                                   2103
```

<210> SEQ ID NO 11
<211> LENGTH: 500
<212> TYPE: PRT
<213> ORGANISM: Homo sapiens

<400> SEQUENCE: 11

Met Ala Trp Ala Ala Leu Leu Gly Leu Leu Ala Ala Leu Leu Leu Leu
1               5                   10                  15

Leu Leu Leu Ser Arg Arg Arg Thr Arg Arg Pro Gly Glu Pro Pro Leu
            20                  25                  30

```
Asp Leu Gly Ser Ile Pro Trp Leu Gly Tyr Ala Leu Asp Phe Gly Lys
        35                  40                  45

Asp Ala Ala Ser Phe Leu Thr Arg Met Lys Glu Lys His Gly Asp Ile
 50                  55                  60

Phe Thr Ile Leu Val Gly Gly Arg Tyr Val Thr Val Leu Leu Asp Pro
 65                  70                  75                  80

His Ser Tyr Asp Ala Val Val Trp Glu Pro Arg Thr Arg Leu Asp Phe
                 85                  90                  95

His Ala Tyr Ala Ile Phe Leu Met Glu Arg Ile Phe Asp Val Gln Leu
                100                 105                 110

Pro His Tyr Ser Pro Ser Asp Glu Lys Ala Arg Met Lys Leu Thr Leu
                115                 120                 125

Leu His Arg Glu Leu Gln Ala Leu Thr Glu Ala Met Tyr Thr Asn Leu
130                 135                 140

His Ala Val Leu Leu Gly Asp Ala Thr Glu Ala Gly Ser Gly Trp His
145                 150                 155                 160

Glu Met Gly Leu Leu Asp Phe Ser Tyr Ser Phe Leu Leu Arg Ala Gly
                165                 170                 175

Tyr Leu Thr Leu Tyr Gly Ile Glu Ala Leu Pro Arg Thr His Glu Ser
                180                 185                 190

Gln Ala Gln Asp Arg Val His Ser Ala Asp Val Phe His Thr Phe Arg
                195                 200                 205

Gln Leu Asp Arg Leu Leu Pro Lys Leu Ala Arg Gly Ser Leu Ser Val
210                 215                 220

Gly Asp Lys Asp His Met Cys Ser Val Lys Ser Arg Leu Trp Lys Leu
225                 230                 235                 240

Leu Ser Pro Ala Arg Leu Ala Arg Arg Ala His Arg Ser Lys Trp Leu
                245                 250                 255

Glu Ser Tyr Leu Leu His Leu Glu Glu Met Gly Val Ser Glu Glu Met
                260                 265                 270

Gln Ala Arg Ala Leu Val Leu Gln Leu Trp Ala Thr Gln Gly Asn Met
                275                 280                 285

Gly Pro Ala Ala Phe Trp Leu Leu Phe Leu Leu Lys Asn Pro Glu
290                 295                 300

Ala Leu Ala Ala Val Arg Gly Glu Leu Glu Ser Ile Leu Trp Gln Ala
305                 310                 315                 320

Glu Gln Pro Val Ser Gln Thr Thr Thr Leu Pro Gln Lys Val Leu Asp
                325                 330                 335

Ser Thr Pro Val Leu Asp Ser Val Leu Ser Glu Ser Leu Arg Leu Thr
                340                 345                 350

Ala Ala Pro Phe Ile Thr Arg Glu Val Val Asp Leu Ala Met Pro
                355                 360                 365

Met Ala Asp Gly Arg Glu Phe Asn Leu Arg Arg Gly Asp Arg Leu Leu
370                 375                 380

Leu Phe Pro Phe Leu Ser Pro Gln Arg Asp Pro Glu Ile Tyr Thr Asp
385                 390                 395                 400

Pro Glu Val Phe Lys Tyr Asn Arg Phe Leu Asn Pro Asp Gly Ser Glu
                405                 410                 415

Lys Lys Asp Phe Tyr Lys Asp Gly Lys Arg Leu Lys Asn Tyr Asn Met
                420                 425                 430

Pro Trp Gly Ala Gly His Asn His Cys Leu Gly Arg Ser Tyr Ala Val
                435                 440                 445
```

```
Asn Ser Ile Lys Gln Phe Val Phe Leu Val Leu Val His Leu Asp Leu
        450                 455                 460

Glu Leu Ile Asn Ala Asp Val Glu Ile Pro Glu Phe Asp Leu Ser Arg
465                 470                 475                 480

Tyr Gly Phe Gly Leu Met Gln Pro Glu His Asp Val Pro Val Arg Tyr
                485                 490                 495

Arg Ile Arg Pro
            500

<210> SEQ ID NO 12
<211> LENGTH: 1614
<212> TYPE: DNA
<213> ORGANISM: Homo sapiens

<400> SEQUENCE: 12
gggggcgggg aactttacct gggagtgggc caggccgcca gccccgccag ccccgccagc      60
cccgccagcc ccgcgatggc ttgggccgcg ctcctcggcc tcctggccgc actgttgctg     120
ctgctgctac tgagccgccg ccgcacgcgg cgacctggtg agcctcccct ggacctgggc     180
agcatcccct ggttggggta tgccttggac tttggaaaag atgctgccag cttcctcacg     240
aggatgaagg agaagcacgg tgacatcttt actatactgg ttgggggcag gtatgtcacc     300
gttctcctgg acccacactc ctacgacgcg gtggtgtggg agcctcgcac caggctcgac     360
ttccatgcct atgccatctt cctcatggag aggattttttg atgtgcagct ccacattac     420 agccccagtg atgaaaaggc caggatgaaa ctgactcttc tccacagaga gctccaggca     480
ctcacagaag ccatgtatac caacctccat gcagtgctgt gggcgatgc tacagaagca     540 ggcagtggct ggcacgagat gggtctcctc gacttctcct acagcttcct gctcagagcc     600
ggctacctga ctctttacgg aattgaggcg ctgccacgca cccatgaaag ccaggcccag     660
gaccgcgtcc actcagctga tgtcttccac acctttcgcc agctcgaccg gctgctcccc     720
aaactggccc gtggctccct gtcagtgggg gacaaggacc acatgtgcag tgtcaaaagt     780
cgcctgtgga agctgctatc cccagccagg ctggccaggc gggcccaccg gagcaaatgg     840
ctggagagtt acctgctgca cctggaggag atgggtgtgt cagaggagat gcaggcacgg     900
gccctggtgc tgcagctgtg ggccacacag gggaatatgg gtcccgctgc cttctggctc     960
ctgctcttcc ttctcaagaa tcctgaagcc ctggctgctg tccgcggaga gctcgagagt    1020
atcctttggc aagcggagca gcctgtctcg cagacgacca ctctcccaca gaaggttcta    1080
gacagcacac ctgtgcttga tagcgtgctg agtgagagcc tcaggcttac agctgccccc    1140
ttcatcaccc gcgaggttgt ggtggacctg gccatgccca tggcagacgg gcgagaattc    1200
aacctgcgac gtggtgaccg cctcctcctc ttccccttcc tgagccccca gagagaccca    1260
gaaatctaca cagacccaga ggtatttaaa tacaaccgat tcctgaaccc tgacggatca    1320
gagaagaaag acttttacaa ggatgggaaa cggctgaaga attacaacat gccctggggg    1380
gcggggcaca atcactgcct ggggaggagt tatgcggtca acagcatcaa caatttgtg    1440 ttccttgtgc tggtgcactt ggacttggag ctgatcaacg cagatgtgga gatccctgag    1500
tttgacctca gcaggtacgg cttcggtctg atgcagccgg aacacgacgt gcccgtccgc    1560
taccgcatcc gcccatgaca cagggagcag atggatccac gtgctcgcct ctgc          1614
```